US007857860B2

(12) United States Patent
Saini et al.

(10) Patent No.: US 7,857,860 B2
(45) Date of Patent: Dec. 28, 2010

(54) BONE VOID FILLER AND METHOD OF MANUFACTURE

(75) Inventors: Sunil Saini, Plainsboro, NJ (US); Jonathan McGlohorn, Pomaria, SC (US); Qing Liu, Hillsborough, NJ (US); Mahesh Krishnan, Stony Point, NY (US); Jaedeok Yoo, East Windsor, NJ (US); Thomas George West, Lawrenceville, NJ (US)

(73) Assignee: Therics, LLC, Akron, OH (US)

( * ) Notice: Subject to any disclaimer, the term of this patent is extended or adjusted under 35 U.S.C. 154(b) by 677 days.

(21) Appl. No.: 10/837,541

(22) Filed: Apr. 30, 2004

(65) Prior Publication Data

US 2005/0027366 A1      Feb. 3, 2005

Related U.S. Application Data

(60) Provisional application No. 60/466,884, filed on Apr. 30, 2003, provisional application No. 60/512,373, filed on Oct. 17, 2003.

(51) Int. Cl.
*A61F 2/28* (2006.01)
(52) U.S. Cl. .................................. 623/23.56
(58) Field of Classification Search .............. 623/16.11, 623/18.11, 17.11–17.16, 23.51, 23.56, 23.61
See application file for complete search history.

(56) References Cited

U.S. PATENT DOCUMENTS

| | | | |
|---|---|---|---|
| 4,743,256 A * | 5/1988 | Brantigan .................... 128/898 |
| 5,141,510 A * | 8/1992 | Takagi et al. .............. 623/23.56 |
| 5,676,700 A | 10/1997 | Black | |
| 6,030,636 A | 2/2000 | Randolph et al. | |
| 6,149,689 A * | 11/2000 | Grundei ..................... 623/23.5 |
| 6,206,924 B1 | 3/2001 | Timm | |
| 6,235,225 B1 | 5/2001 | Okada | |

(Continued)

FOREIGN PATENT DOCUMENTS

WO      WO 92/15440      9/1992

(Continued)

OTHER PUBLICATIONS

Database WPI Section Ch, Week 198709, Derwent Publications, London, GB; XP-002298096, AN 1987-059508.

(Continued)

*Primary Examiner*—Anu Ramana
(74) *Attorney, Agent, or Firm*—Middleton Reutlinger; Robert H. Eichenberger; Eric L. Killmeier

(57) ABSTRACT

Bone void filler pieces that are conducive to packing or nesting when a plurality of pieces are located in a cavity in random orientation. The bone void filler of the present invention includes a higher bulk packing density and a porosity of less than 80% to provide a better match native bone ingrowth rate. Further, the bone void filler includes a bi-modal pore distribution with a high frequency of smaller pores to enhance the density characteristic of the bone void filler pieces. A method of manufacturing the bone void filler pieces includes a precursor powder composition suitable to form a ceramic matrix; the preform is converted by chemical reaction to a final composition. The preform further includes the use of a porogen that decomposes to gaseous decomposition products upon heating.

59 Claims, 32 Drawing Sheets

U.S. PATENT DOCUMENTS

| | | |
|---|---|---|
| 6,294,187 B1 | 9/2001 | Boyce |
| 6,383,519 B1 * | 5/2002 | Sapieszko et al. ............ 424/489 |
| 6,391,059 B1 | 5/2002 | Lemperle |
| 6,458,162 B1 * | 10/2002 | Koblish et al. ............ 623/23.51 |
| 6,599,516 B1 * | 7/2003 | Knaack ....................... 424/423 |
| 6,630,152 B2 * | 10/2003 | Chou ......................... 424/402 |
| 6,630,153 B2 | 10/2003 | Long et al. |
| 6,767,369 B2 * | 7/2004 | Boyer et al. .............. 623/23.63 |
| 7,393,883 B2 * | 7/2008 | Jones et al. ................. 523/116 |
| 2003/0055511 A1 | 3/2003 | Schryver et al. |
| 2003/0082232 A1 * | 5/2003 | Lee et al. .................... 424/484 |
| 2003/0180376 A1 * | 9/2003 | Dalal et al. ................. 424/602 |
| 2004/0019132 A1 | 1/2004 | Long et al. |

FOREIGN PATENT DOCUMENTS

| | | |
|---|---|---|
| WO | WO/02/05750 A2 | 1/2002 |
| WO | 03024316 A2 | 3/2003 |

OTHER PUBLICATIONS

Enomoto, "*Filler for Deficient Part and Cavity of Bone and Production Thereof*," Patent Abstracts of Japan, vol. 0133, No. 79 (C-628), Aug. 22, 1989, JP 1 131082 published May 23, 1989.

* cited by examiner

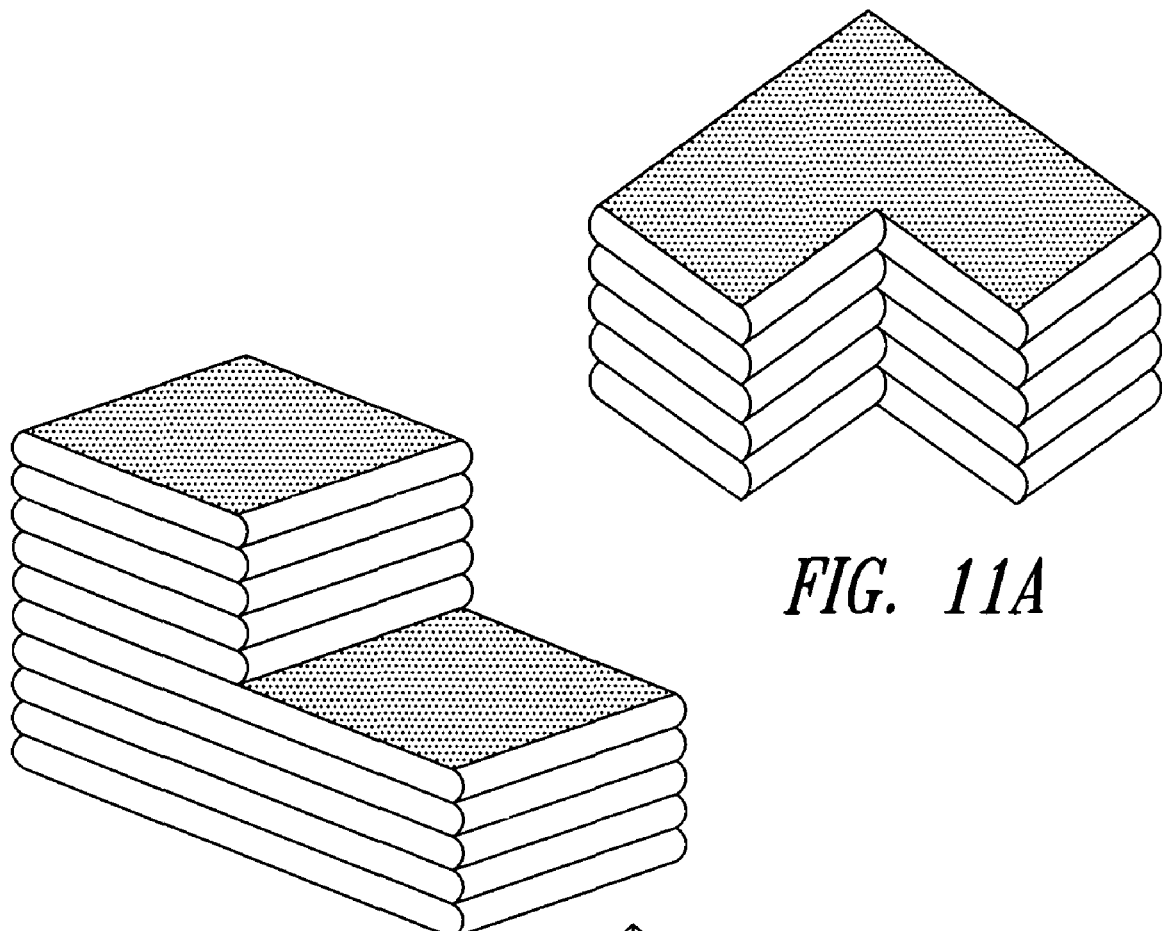
*FIG. 11A*
*FIG. 11B*
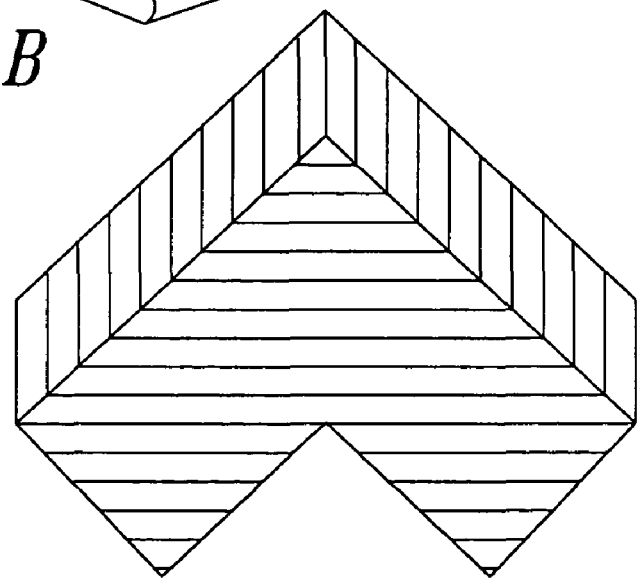
*FIG. 11C*

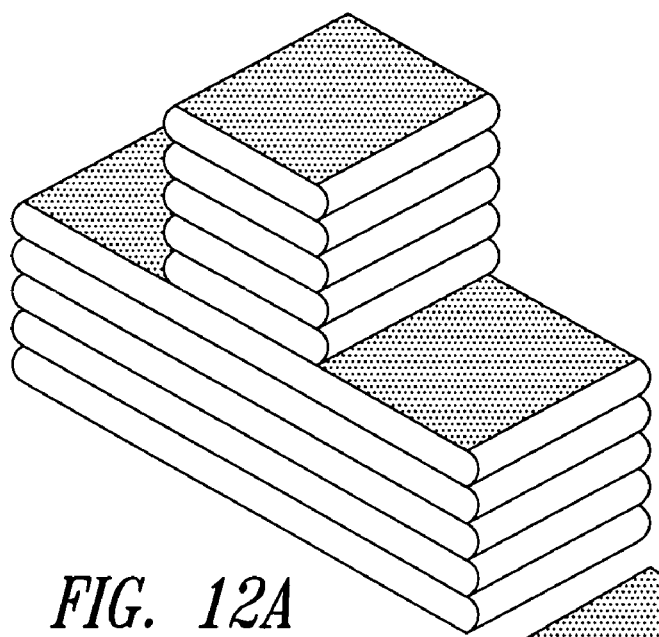
*FIG. 12A*
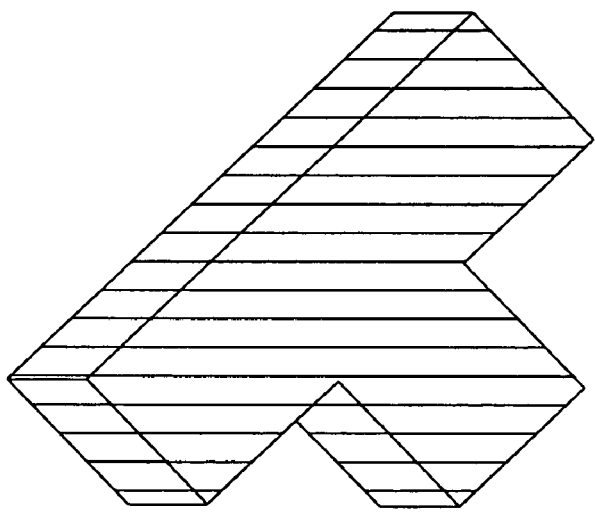
*FIG. 12B*
*FIG. 12C*

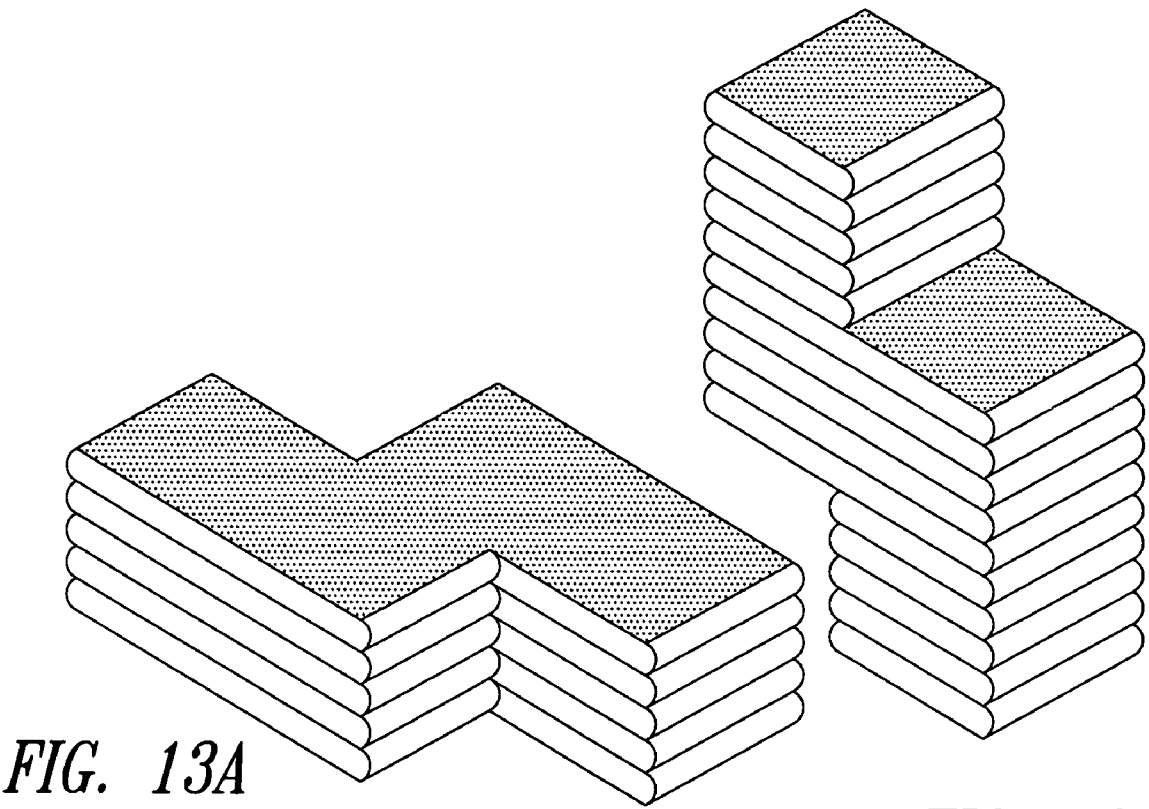
FIG. 13A
FIG. 13B
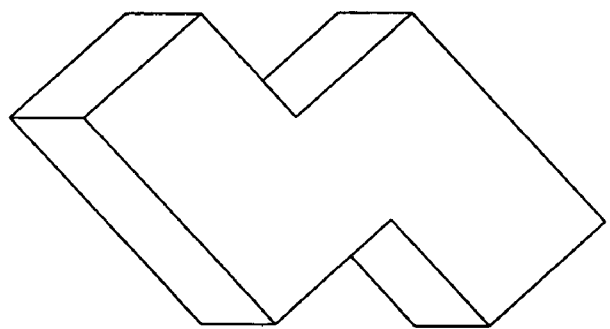
FIG. 13C

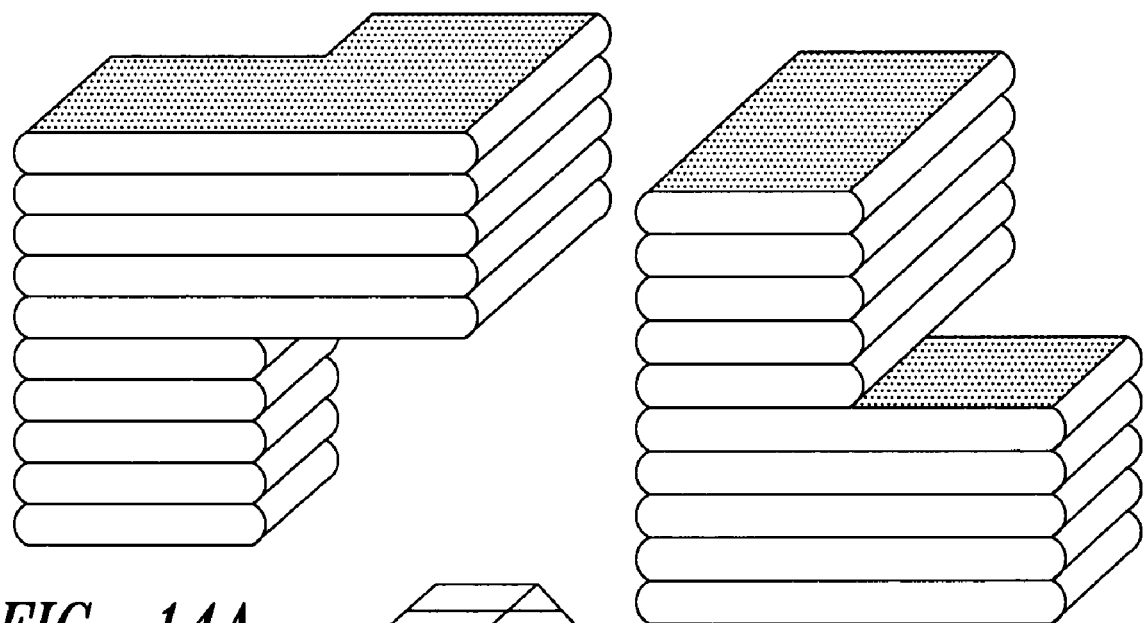
FIG. 14A
FIG. 14B
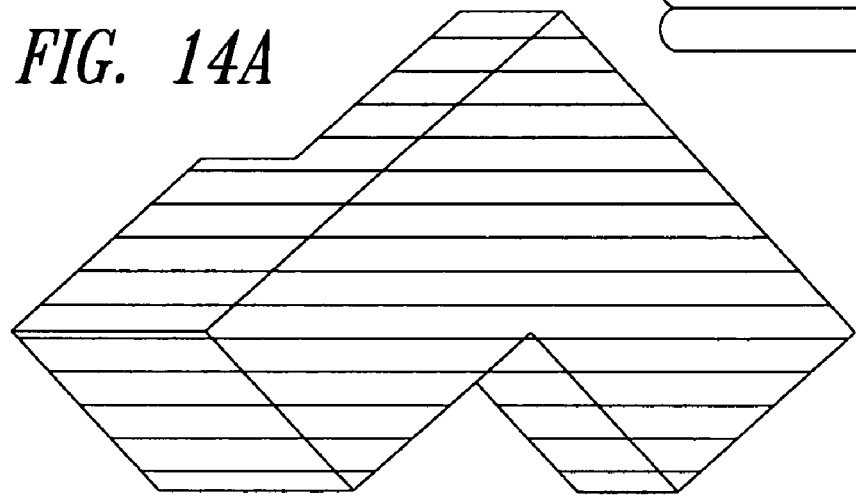
FIG. 14C

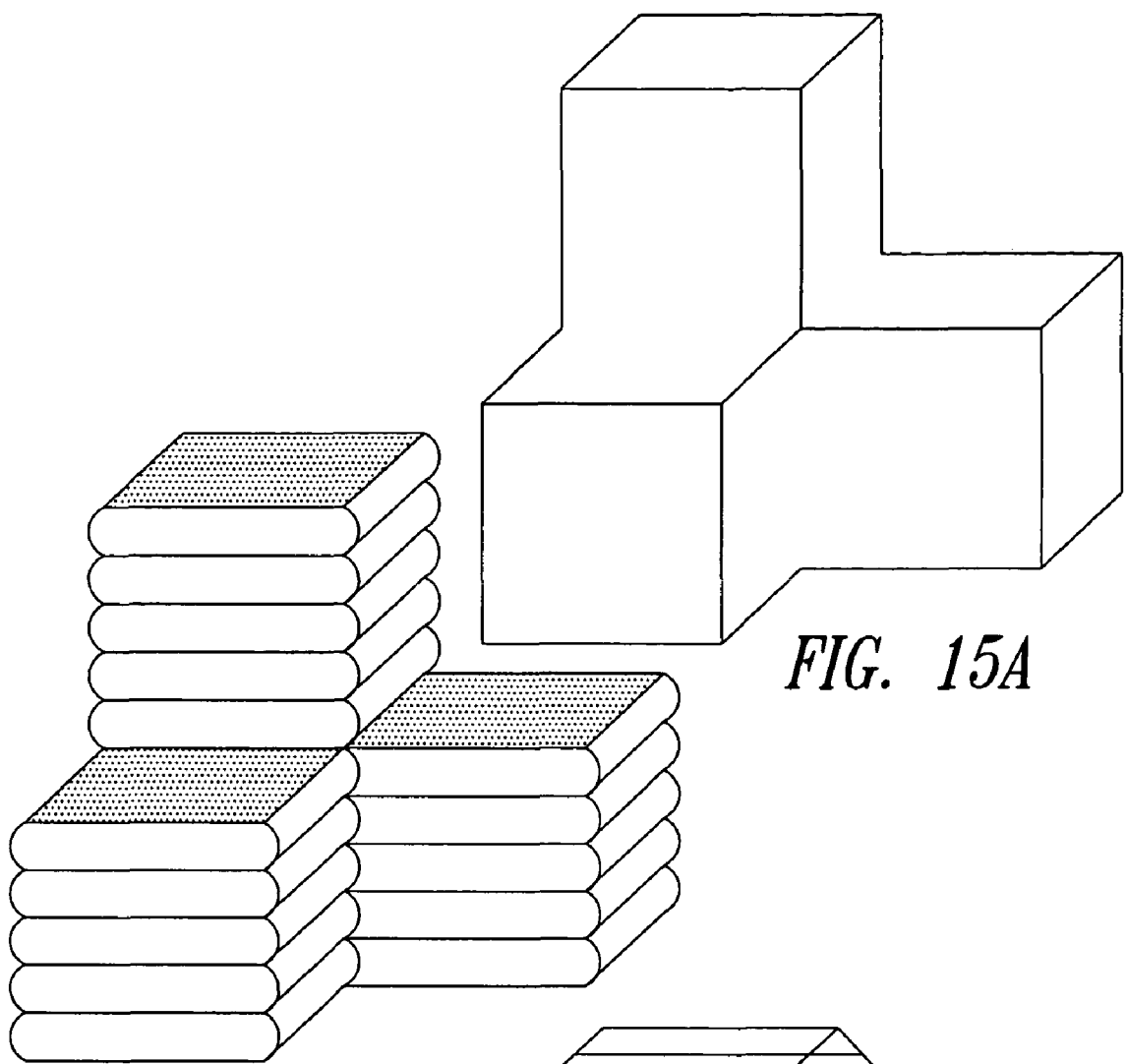
*FIG. 15A*
*FIG. 15B*
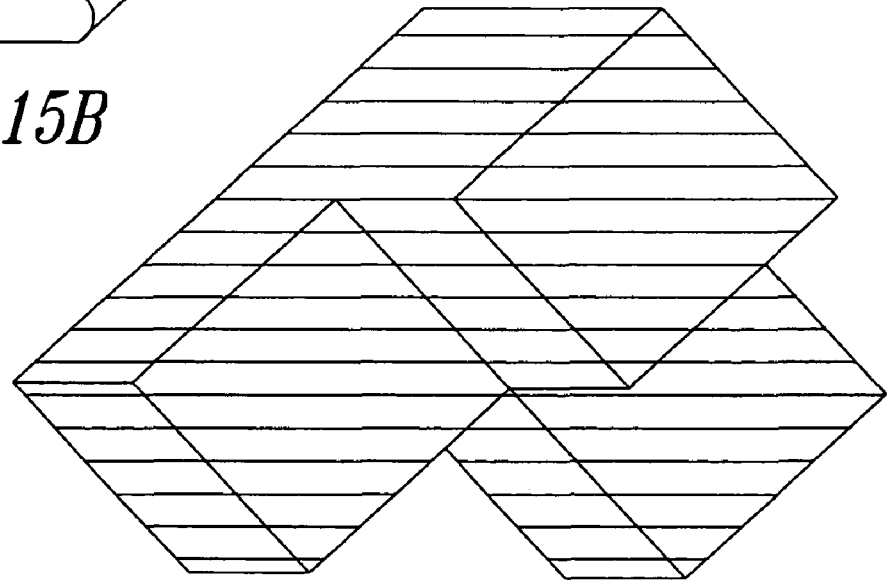
*FIG. 15C*

US 7,857,860 B2

BONE VOID FILLER AND METHOD OF MANUFACTURE

CROSS-REFERENCE TO RELATED APPLICATIONS

This application claims the benefit of Provisional Application filed Apr. 30, 2003, titled "Bone Void Filler and Method of Manufacture", application No. 60/466,884, and Provisional Application filed Oct. 17, 2003, titled "Additional Shapes and Other Details of Bone Void Filler Pieces," application No. 60/512,373; each of which is incorporated herein by reference in its entirety.

BACKGROUND OF THE INVENTION

1. Field of the Invention

The present invention relates to a bone void filler, and more particularly, a bone void filler having a designed shape, porosity, pore distribution and material composition to provide enhanced bone healing and ingrowth, and a method of manufacturing the bone void filler.

2. Description of the Related Art

Bone fractures and defects can be difficult to heal in certain circumstances. If a defect or gap is larger than a certain critical size, natural bone is unable to bridge or fill the defect or gap. Accordingly, it is of interest to fill such voids with a substance, traditionally referred to as a bone void filler, which helps the void to eventually fill with naturally grown bone. The bone void filler may be a collection of pieces of either random or designed shape. Existing bone void filler products include a product called Vitoss made by OrthoVita (Malvern, Pa.), and a product called ProOsteon made by Interpore. A known shape of bone void filler piece is jacks or tetrapods under the product name OsteoSet or Jax made by Wright Medical. The shape of the Vitoss product pieces is random, formed by fracturing (comminuting) larger porous pieces. The Jax product is formed by powder compaction.

As far as material composition, bone void fillers have been both resorbable and nonresorbable. Among the calcium-phosphorus compounds that resemble the mineral content natural bone are hydroxyapatite, beta-tricalcium-phosphate, alpha-tricalcium-phosphate and the like.

Among the factors which are believed to contribute to making a good bone void filler material are the proper time scale for the bone void filler to resorb or decompose in the human body, the proper size and distribution of pores in the bone void filler, the proper void fraction, and a suitable surface geometry. Ultimately, the criterion for a good bone void filler may be the amount and quality of natural bone that eventually grows in and among and in place of the bone void filler owing in large part to the configuration of the bone void filler.

Accordingly, it would be desirable to create a bone void filler which does a better job of inducing the growth of natural bone to fill a defect of void. To this end, it would be desirable to create a bone void filler that is a collection of pieces each of which has a shape which lends itself to packing to a fairly large geometric packing density of the overall pieces. It is also desirable to create a bone void filler that has characteristics of easy handling and placement for the surgeon. It may also be desirable that the bone void filler pieces have certain surface geometry or roughness features on at least some of their surfaces. It may also be desirable to create a bone void filler which has a somewhat narrow pore size distribution. It may be desirable that the bone void filler be made largely of resorbable material. It may be desirable to provide both osteoconductive and osteoinductive properties of the bone void filler.

SUMMARY OF THE INVENTION

The invention comprises a plurality of bone void filler pieces. The bone void filler pieces may have a cruciform prismatic shape having dimensions which are conducive to packing or nesting when a plurality of the pieces are located in a cavity in random orientations with respect to each other. Two approximately parallel surface planes separated by a prismatic dimension may bound the cruciform prismatic shape. On some of its surfaces the bone void filler pieces may comprise at least some ridges that may be approximately parallel to the edges of the bone void filler piece. On other surfaces the bone void filler pieces may comprise random isotropic roughness. The bone void filler may be resorbable and may comprise a significant fraction of tricalcium phosphate, of either or both possible crystal structures. Other shapes, such as T, L, Z and others, are also possible. Mixtures of sizes and shapes are possible of these pieces, as is mixing with particles of demineralized bone matrix. The bone void filler may have a particular set of characteristics regarding size of pores and overall density when packed into a void, those characteristics being chosen to be advantageous for promoting the ingrowth of natural bone.

The invention further comprises a method of making such bone void filler. The method may include three-dimensional printing. The method may include starting from a powder composition containing precursors which are suitable to form product ceramic by chemical reaction at an appropriate temperature. The method may include the use of a porogen that decomposes to gaseous decomposition products. The invention further comprises bone void filler made by three-dimensional printing and bone void filler made by the chemical reaction.

BRIEF DESCRIPTION OF THE FIGURES

FIGS. 11A-C are schematic illustrations of L-shaped bone void filler pieces in accordance with principles of the present invention.

FIGS. 12A-C are schematic illustrations of T-shaped bone void filler pieces in accordance with principles of the present invention.

FIGS. 13A-C are schematic illustrations of bone void filler pieces having a shape that may be described as a Z in accordance with principles of the present invention.

FIGS. 14A-C are schematic illustrations of bone void filler pieces having a shape that may be described as an out-of-plane Z in accordance with principles of the present invention.

FIGS. 15A-C are schematic illustrations of a bone void filler piece having a shape that may be described as a corner piece in accordance with principles of the present invention.

DETAILED DESCRIPTION OF THE INVENTION

Three-dimensional printing (3DP) has begun to be used to make medical products including bone substitute materials. The ability of 3DP to deposit specific quantities and compositions of material in specific places has provided the ability to design and manufacture such articles in a detailed way which has not been achievable with other dosage form manufacturing techniques. Three-dimensional printing has not yet been put to use for making bone void filler, with the result that the control of architecture at various size scales and other advantages of three-dimensional printing have not yet been available for the manufacturing of bone void filler until the present invention.

The invention comprises a plurality of bone void filler pieces that are similar in shape and dimensional size distribution to each other; alternatively, the bone void filler pieces may include a variety of preselected shaped pieces or may include random shapes intermixed with preselected shapes. The bone void filler pieces may have dimensions which are conducive to packing or nesting when a plurality of the pieces are located in a cavity in random orientations with respect to each other.

One embodiment of the present invention includes bone void filler pieces having a cruciform shape; the cruciform shape may have four arms each connected to a central region in a coplanar manner. The arms may be approximately identical to each other and may be spaced at intervals of approximately 90 degrees from neighboring arms. The arms may be approximately rectangular in plan view.

Figure 1:
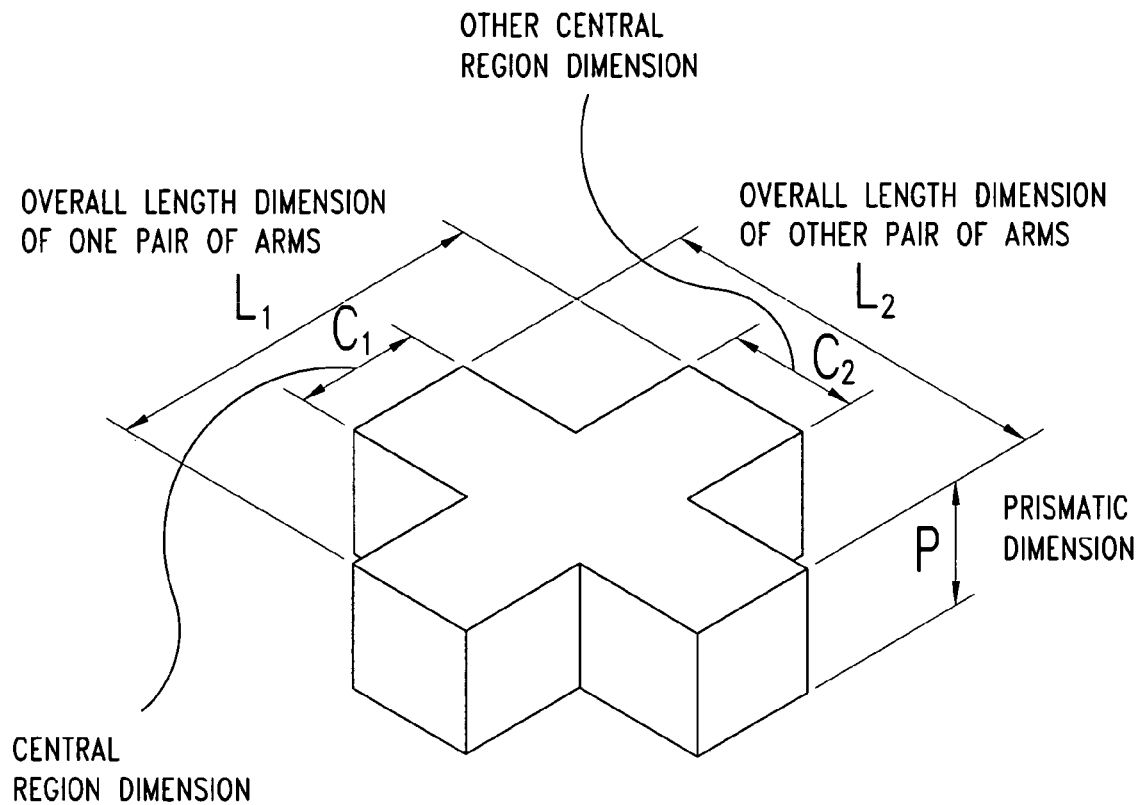
FIG. 1 illustrates a schematic of a bone void filler piece in the shape of a cruciform, including definition of dimensions, in accordance with principles of the present invention.

The embodiment of this shape is illustrated in FIG. 1, including definition of dimensions. As shown in FIG. 1, $L_1$ is the overall length dimension of a pair of arms in a first direction and $L_2$ is the overall length dimension of a pair of arms in a second direction. $C_1$ is the central region dimension in a first direction, and $C_2$ is the central region dimension in a second direction. P is the prismatic dimension.

The cruciform shape may be symmetric in the sense that the overall arm length dimension of one opposed pair of arms may be at least approximately the same as the overall arm length dimension of the other opposed pair of arms. It may be considered that the overall arm length dimensions may be within 20% of each other. The central region may have a central region dimension. The central region dimension in one direction may be within 20% of the central region in the other direction. The central region dimension may be approximately one-third of the overall arm length dimension, with a possible range being from 20% to 45% of the overall arm length dimension.

The bone void filler pieces may be prismatic in the sense that they may be bounded by two approximately parallel planes which are separated by a prismatic distance, i.e., the dimension perpendicular to the plane in which the cruciform shape lies. This prismatic distance may be chosen to be between 25% and 65% of the overall arm length.

It is believed, although it is not wished to be restricted to this explanation, that the ratios discussed above (relating the overall arm length, the central region dimension and the prismatic dimension) may be helpful for achieving a relatively large geometric packing density for the overall shape when pieces having this shape and proportion are randomly stacked such as after being placed into a void in a bone. This geometric packing fraction refers to the fitting together of the overall external shapes of the bone void filler pieces, with no reference to any internal porosity that may exist inside those shapes.

Figure 2:
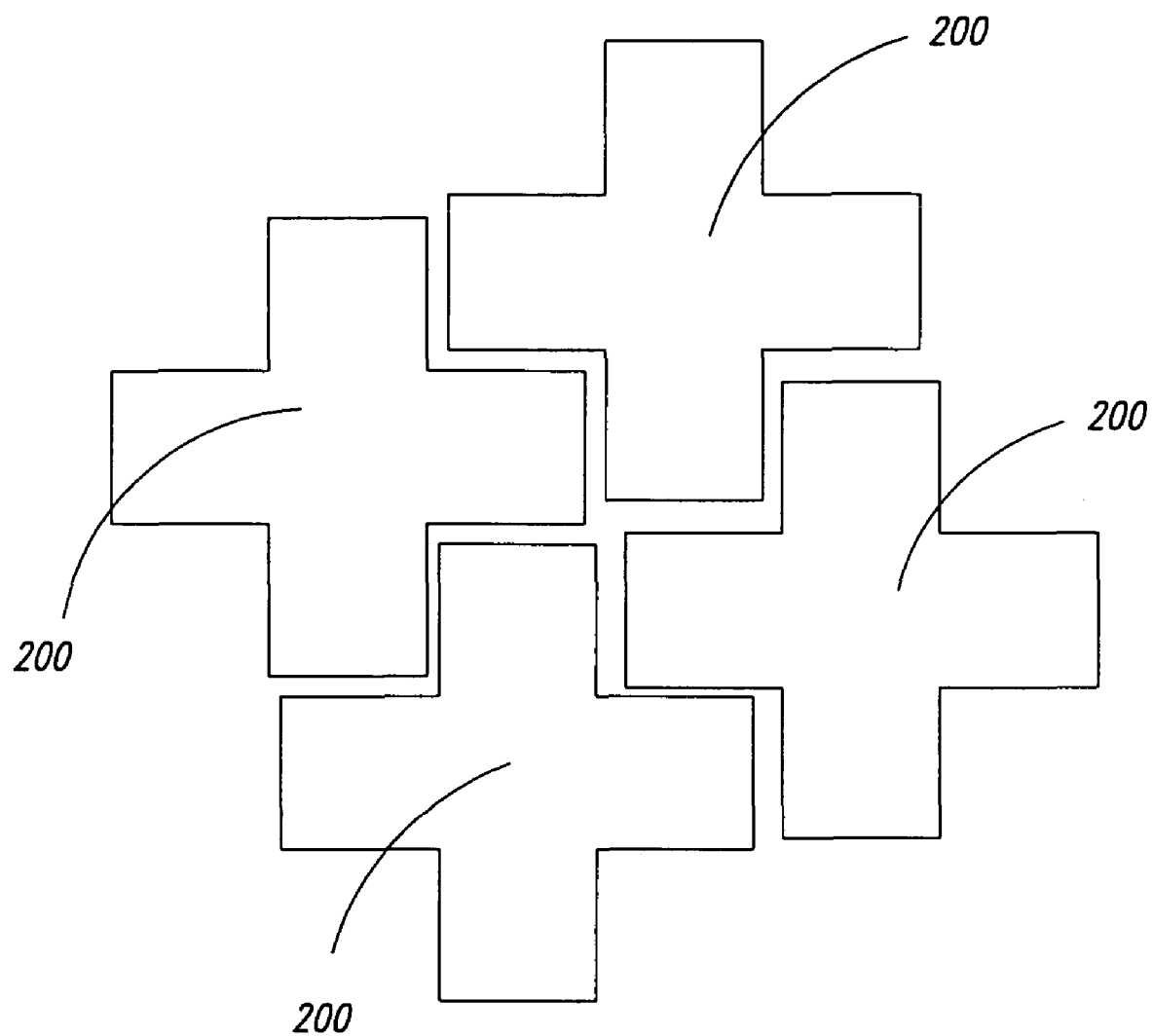
FIG. 2 shows a possible packing arrangement of a plurality of cruciform bone void filler pieces of the type shown in FIG. 1 in accordance with principles of the present invention.

It is true that bone void filler pieces 200 will not necessarily arrange themselves all in a plane, but as a simple case, if they did arrange themselves in a plane, the bone void filler pieces of the present invention could occupy a plane in a fairly dense geometric packing arrangement as shown in FIG. 2.

Figure 3:
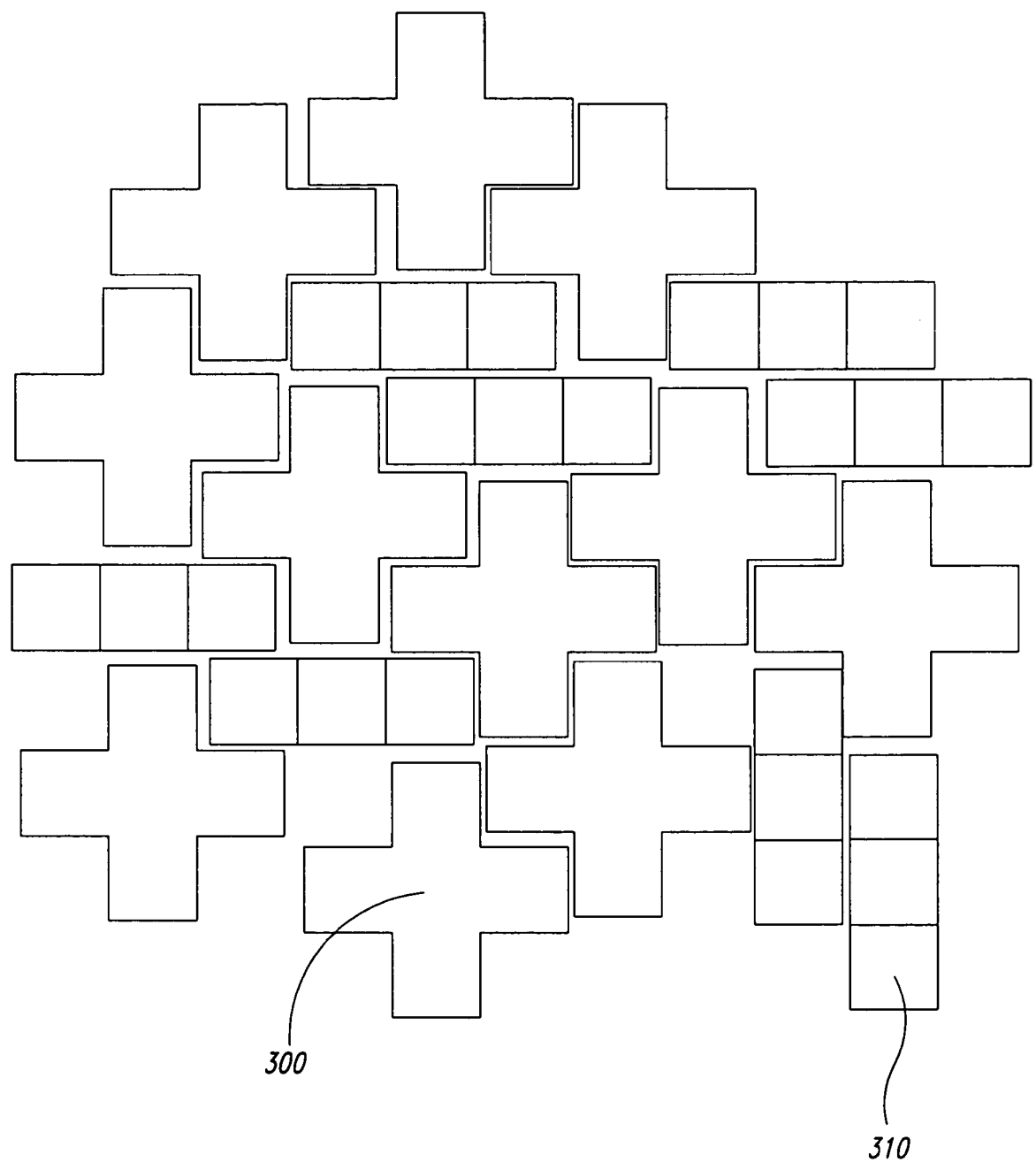
FIG. 3 illustrates another possible packing arrangement of the cruciform bone void filler pieces, involving a greater degree of randomness in accordance with principles of the present invention.

It is also true that bone void filler pieces will not necessarily arrange themselves strictly in only two mutually perpendicular orientations, but as a slightly more complicated case than the previous illustration while still being a simplified case, another possible packing arrangement is shown in FIG. 3. In this Figure, some of the bone void filler pieces 310 are shown in side view while most of the bone void filler pieces 300 are shown in plan view such that the cruciform shape is visible. Although this packing is not as dense as in the previous Figure, because there are occasional "holes," still this accomplishes a geometric packing arrangement that is fairly dense.

Figure 4:
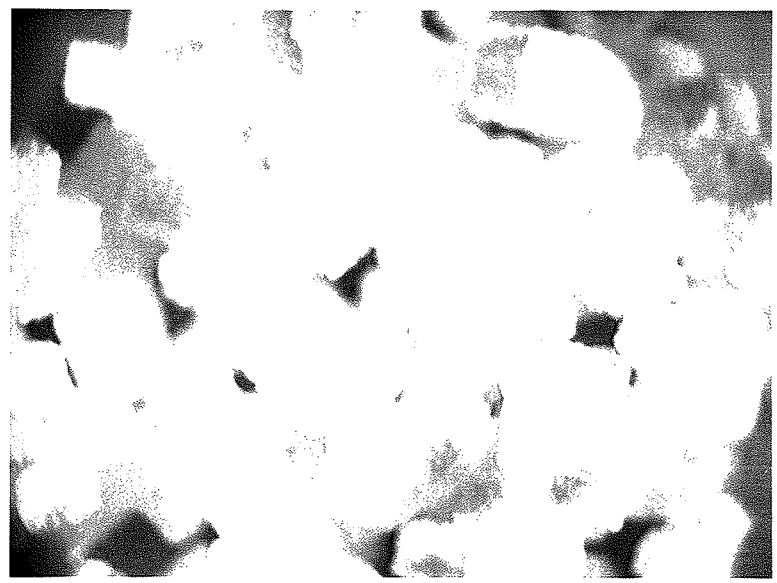
FIG. 4 is a photograph of an aggregate of cruciform shaped bone void filler pieces in a random packing arrangement in accordance with principles of the present invention.

Finally, the packing of the bone void filler pieces may be still more random involving all three dimensions. This is illustrated in FIG. 4. While it is not possible to give the geometric packing a more specific description due to the random nature of the orientations, still it is believed that the geometric packing has a good efficiency for overall volume being occupied by the described shapes. The described shapes may interlock with each other, which is believed to be good for stability while healing and bone ingrowth are taking place in an actual patient. Even when the bone void filler shapes are randomly oriented with respect to each other in all three dimensions, the maximum dimension of space between them may still be less than a critical dimension for bone regrowth that can be bridged by natural bone.

Figure 5:
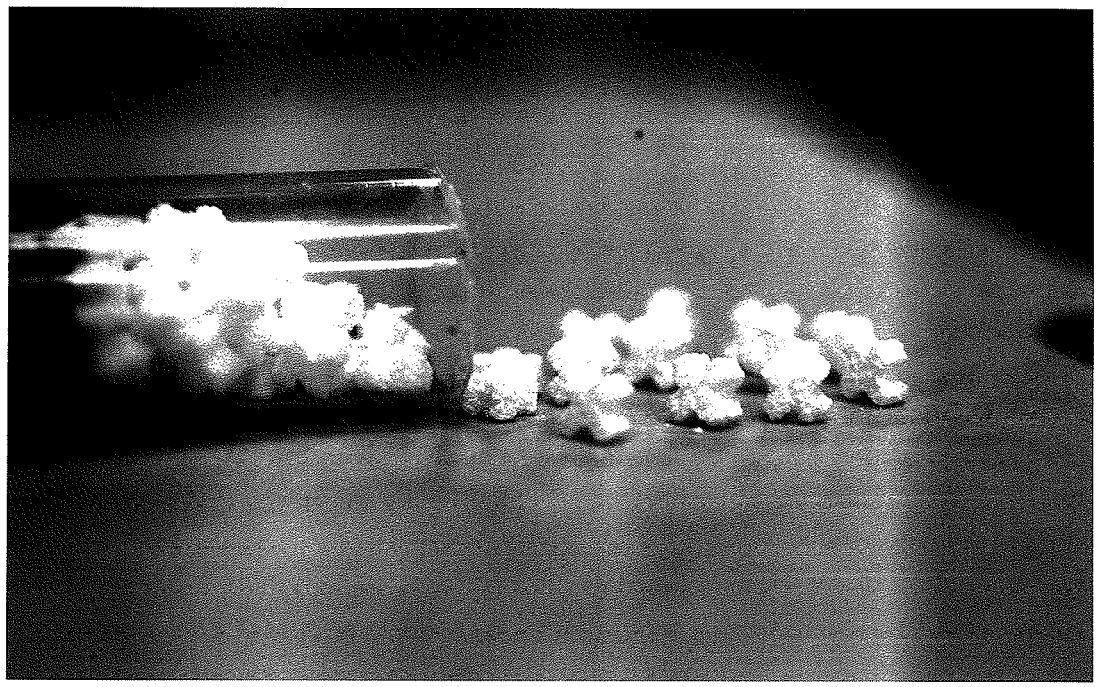
FIG. 5 is a photograph of a vial of cruciform shaped bone void filler pieces in accordance with principles of the present invention.

FIG. 5 shows actual bone void filler pieces of the present invention in a random orientation in and spilling out of a jar.

Figure 6:
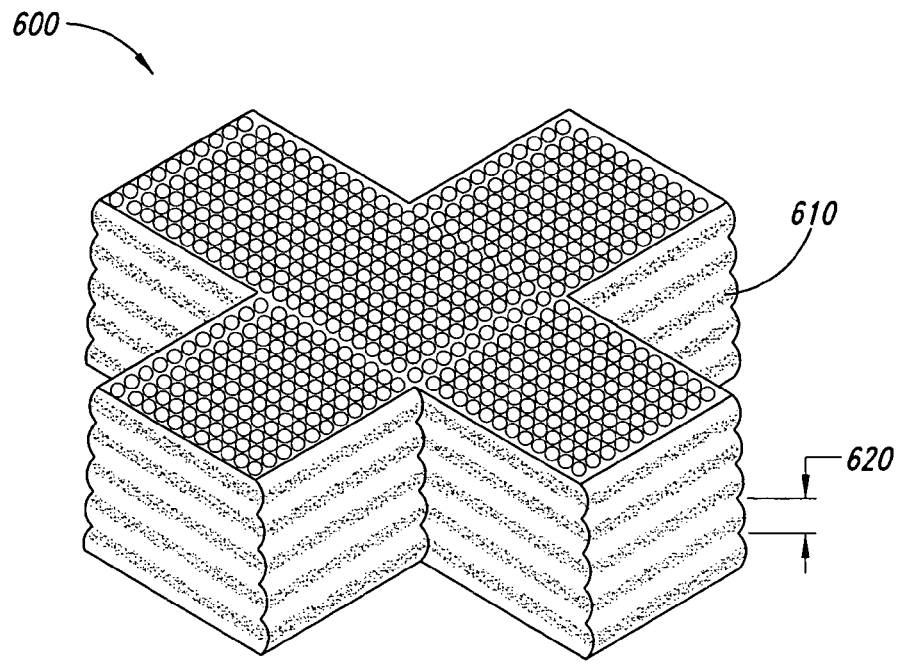
FIG. 6 illustrates ridges on side surfaces of a cruciform shaped bone void filler piece in accordance with principles of the present invention.

As shown in FIG. 6, another property which the bone void filler piece 600 may have is a geometric feature or pattern on various surfaces. The perimetral surfaces 610 may be considered to be the surfaces that trace out the sides of cross shape, as illustrated in FIG. 6. These are the surfaces that, in the orientation illustrated, face in a horizontal direction. The cruciform bone void filler may comprise, on its perimetral surfaces, at least some ridges which are parallel to the surface plane and may extend around at least a portion of the perimeter of the bone void filler piece. In general, surface irregularity is believed to be conducive to bone formation and ingrowth, and such ridges may serve that purpose.

The dimension of a ridge 620 in a direction along the prismatic direction may be approximately the thickness of a layer of powder used in the manufacturing process described elsewhere herein. The dimension of a ridge transverse to the ridge itself may be approximately 400 micrometers, or, more generally, in the range of 100 to 800 micrometers. The dimension of such a ridges along the prismatic direction may be approximately one-seventh of the prismatic dimension of the bone void filler piece, or more generally, between one-third and one-fifteenth of the prismatic dimension of the bone void filler piece.

It is not necessary that the perimetral surfaces of the bone void filler piece have such ridges or have such ridges everywhere. However, at least some such ridges may be present on at least a portion of some perimetral surfaces. The ridges may, in cross-section of the ridge, have a somewhat scalloped shape having a scallop-to-scallop width as just described and having a depth (a trough-to-crest distance) that may be less than the scallop-to-scallop width. The cross-section of a ridge can vary somewhat randomly and even if a ridge exists in some places on a given surface it does not have to exist everywhere on that surface.

The surfaces of the bone void filler piece that do not have ridges, which in the orientation shown are the surface planes, may have roughness that is approximately isotropic and random in nature. A root mean square dimension of surface roughness may describe this roughness, which may be in the range of 20 micrometers to 200 micrometers.

In the preceding Figures, the description of which type of surface pattern is found where can be described as for the orientation shown, the ridges are possible on any surface which faces in a horizontal direction and the random roughness is possible on any surface which faces in a vertical direction.

Figure 7:
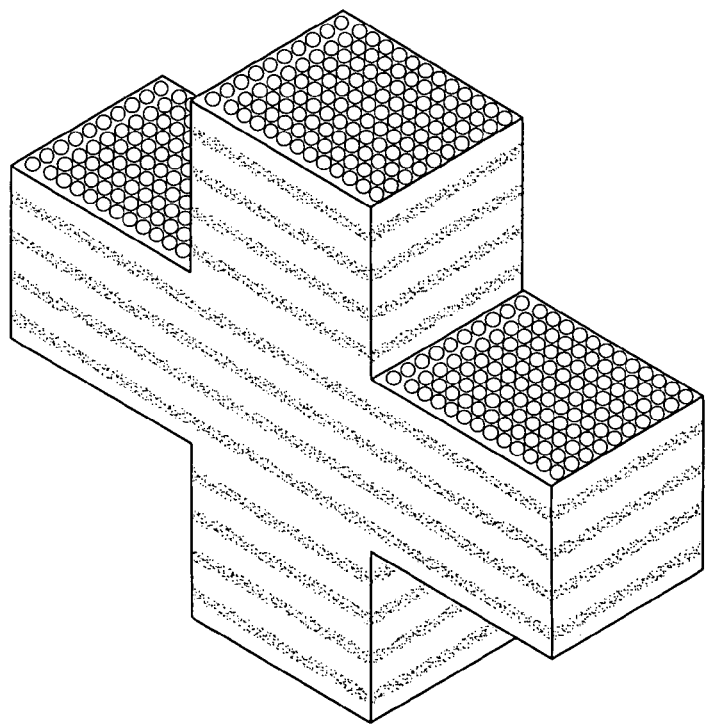
FIG. 7 shows additional possible orientations of a bone void filler piece showing ridges on some surfaces and approximately isotropic roughness on other surfaces in accordance with principles of the present invention.

It is also possible that the choice of which surfaces have ridges and which surfaces have random roughness could be different. It is possible that in the orientation shown in FIG. 7, the ridges can possibly exist on any surface that faces in a horizontal direction and the random roughness is possible on any surface that faces in a vertical direction.

The bone void filler may comprise individual particles, such as of ceramic, partially joined directly to each other. The bone void filler pieces may be porous. In one embodiment of the present invention, the pores have an average pore size of approximately 60 microns and may generally be contained within a range of 1 micrometer to 800 micrometers. A void fraction within an individual bone void filler piece may be defined by considering the overall volume defined by the external surfaces of the bone void filler piece, and comparing the empty space (not occupied by solid material) in the interior of the piece to the overall volume. According to one embodiment of the present invention, the void fraction is approximately 60% to 70%, or, more generally, in the range of 50% to 80%.

Figure 8:
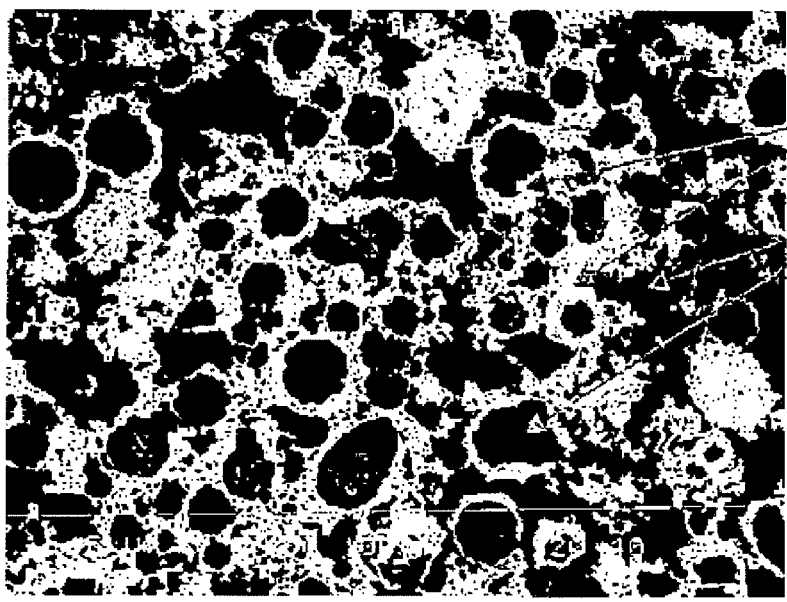
FIG. 8 illustrates an SEM of the microstructure of the bone void filler of the present invention.
Figure 9:
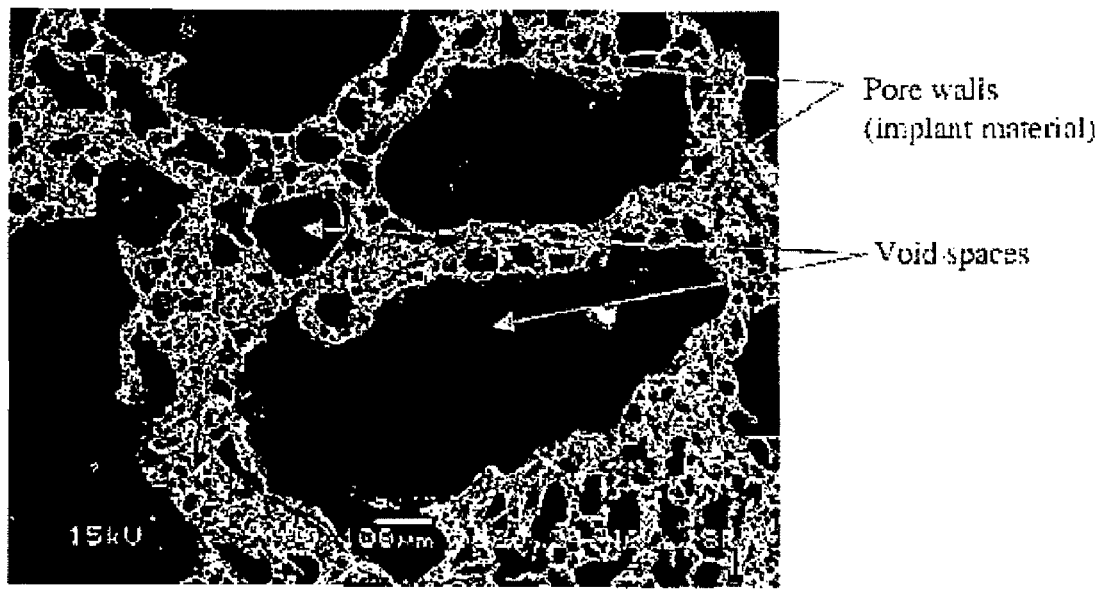
FIG. 9 illustrates an SEM of the microstructure of a prior art bone void filler.

FIG. 8 illustrates the microstructure of the bone void filler of the present invention. FIG. 9 illustrates an SEM of the microstructure of the prior art bone void filler.

The bone void filler may be resorbable and may comprise a significant fraction of tricalcium phosphate. The bone void filler may comprise a significant fraction of beta tricalcium phosphate or a significant fraction of alpha tricalcium phosphate or may comprise both beta tricalcium phosphate and alpha tricalcium phosphate. The bone void filler may comprise at least 75% beta tricalcium phosphate. Substances making up any remaining fraction or the balance may be any other member or members of the calcium phosphate family.

The bone void filler may be sterile and may be packaged suitably to remain sterile until use.

Figure 10A:
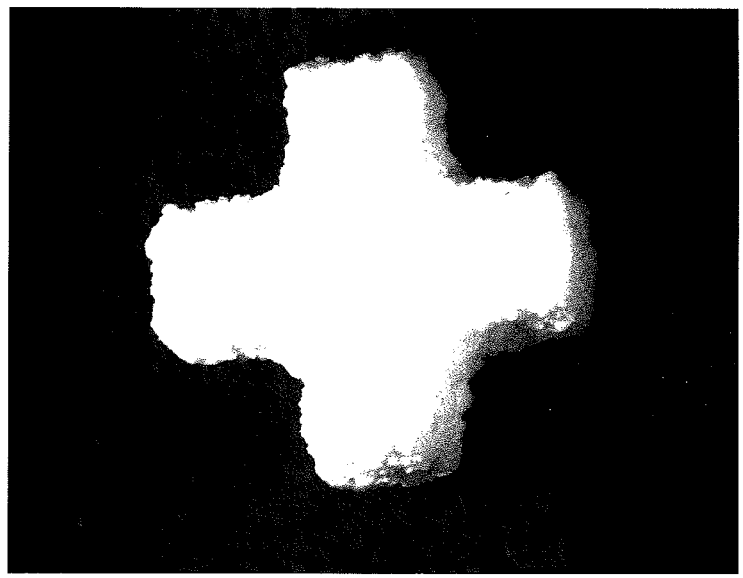
FIG. 10A is a photograph of a bone void filler piece of the present invention.
Figure 10B:
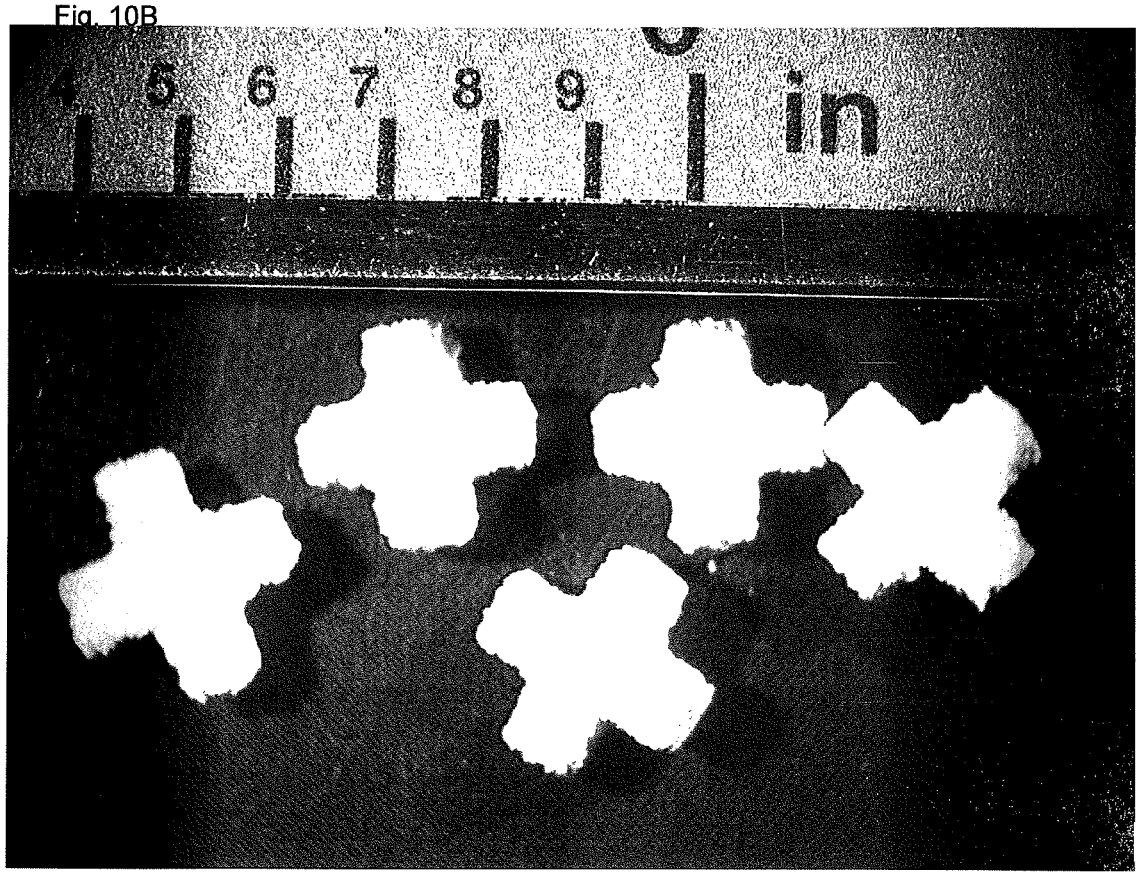
FIG. 10B is a photograph illustrating several bone void filler pieces and also illustrates an exemplary dimensional scale in accordance with principles of the present invention.

FIG. 10A illustrates one bone void filler piece of the present invention. FIG. 10B illustrates several such pieces and also illustrates an exemplary dimensional scale.

Additional Shapes

Additional shapes are shown in the following figures. The additional shapes include L's, T's, Z's, out-of-plane Z's and corner pieces.

First of all, it is possible that any of these shapes may have all of their surfaces of substantially identical texture, which may be substantially isotropic roughness. This is true as well for the cruciform prismatic shapes previously disclosed.

Alternatively, it is possible that some surfaces may have ridges. If there are ridges, for all of the shapes disclosed herein, it is possible that there may be some surfaces (all of which are parallel to each other) that have a non-ridged surface, while all of the other surfaces of the shape may have ridges. For most of these shapes, as illustrated, there are two different possible orientations of the shape, i.e., two different possibilities as far as which surfaces of the bone void filler piece have ridges and which surfaces do not have ridges. Also, it is possible that these same shapes of bone void filler pieces could have ridges on substantially all of their surfaces.

FIGS. 11A-C illustrates an L-shaped bone void filler pieces. A prismatic shape based on an L can be thought of as having a central region with two extensions coming out of it in directions that are co-planar and substantially perpendicular to each other. The extensions may be of substantially constant cross-section along the direction of their extension outward from the central region. In this illustration, the two extensions are substantially identical to each other, although they could be different if desired.

In several of the following figures, one piece shown is a bone void filler piece having substantially identical texture on all its surfaces, and the other illustrated bone void filler pieces have ridges. For the situation in which ridges are present on some but not all surfaces, this illustration shows two different possible orientations as far as which surfaces can have ridges and which surfaces do not have ridges. Surfaces that do not have ridges can have roughness that is approximately isotropic in nature. In the illustrations of bone void filler pieces that have both ridged surfaces and non-ridged surfaces, some surfaces are hidden. Those hidden surfaces that are parallel to the labeled approximately isotropically rough surfaces can also be approximately isotropically rough. It is also possible for such a bone void filler piece to have ridges on substantially all of its surfaces, as illustrated at the bottom of the illustration.

FIGS. 12A-C illustrates T-shaped bone void filler pieces. A prismatic shape based on a T can be thought of as having a central region with three extensions coming out of it, two of the extensions being collinear and one of the extensions in a direction which is substantially perpendicular to the direction of the other two extensions. The extensions may be of substantially constant cross-section along the direction of their extension outward from the central region. In this illustration, the three extensions are substantially identical to each other, although they could be different if desired.

FIGS. 13A-C illustrates bone void filler pieces having a shape that may be described as a Z. A prismatic shape based on a Z can be thought of as having a central region with two extensions coming out of it, the extensions being parallel to each other (and hence co-planar with each other) but not collinear with each other. The extensions may be of substantially constant cross-section along the direction of their extension outward from the central region. In this illustration, the two extensions are substantially identical to each other, although they could be different if desired.

FIGS. 14A-C illustrates bone void filler pieces having a shape that may be described as an out-of-plane Z. An out-of-plane Z can be thought of as having a central region with two extensions coming out of it, with the two extensions being not co-planar with each other. The extensions may be of substantially constant cross-section along the direction of their extension outward from the central region. In this illustration, the two extensions are substantially identical to each other, although they could be different if desired.

FIGS. 15A-C illustrates a bone void filler piece having a shape that may be described as a corner piece. A corner piece can be thought of as having a central region with three extensions coming out of it, with none of the extensions being co-planar with any other extension. The extensions may be of substantially constant cross-section along the direction of their extension outward from the central region. In this illustration, the three extensions are substantially identical to each other, although they could be different if desired.

Figure 16:
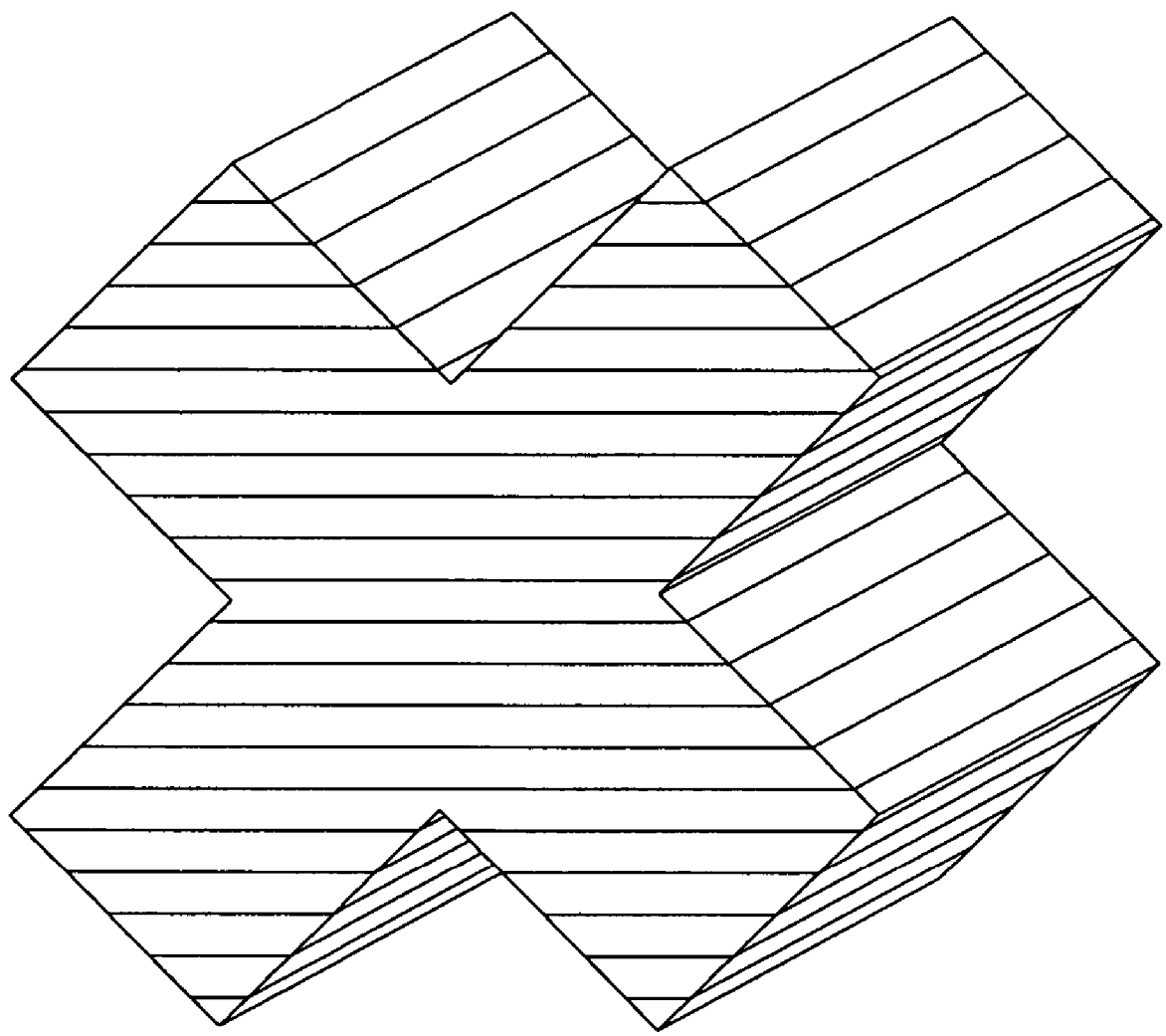
FIG. 16 illustrates a cruciform prismatic bone void filler piece, which has ridges on substantially all of its surfaces in accordance with principles of the present invention.

FIG. 16 illustrates a cruciform prismatic bone void filler piece, which has ridges on substantially all of its surfaces, just as was illustrated herein for the various other shapes.

For those of the described shapes that are prismatic shapes, there can be an aspect ratio that may be defined as the prismatic dimension divided by the largest external dimension from a corner to another corner of the planar shape that forms the base of the prism. This aspect ratio may have a value between approximately 0.2 and 0.5 or, more generally, between 0.1 and 0.7.

Figure 17A:
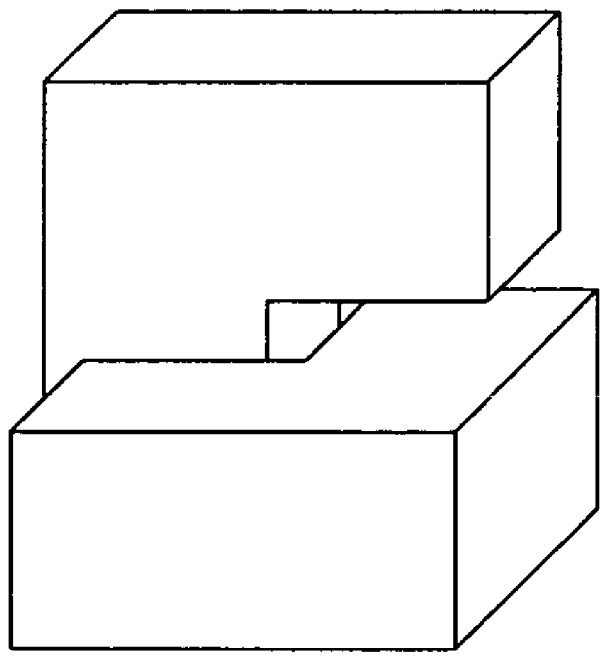
FIGS. 17A and 17B show some possible nesting patterns for L shape bone void filler in accordance with principles of the present invention.
Figure 17B:
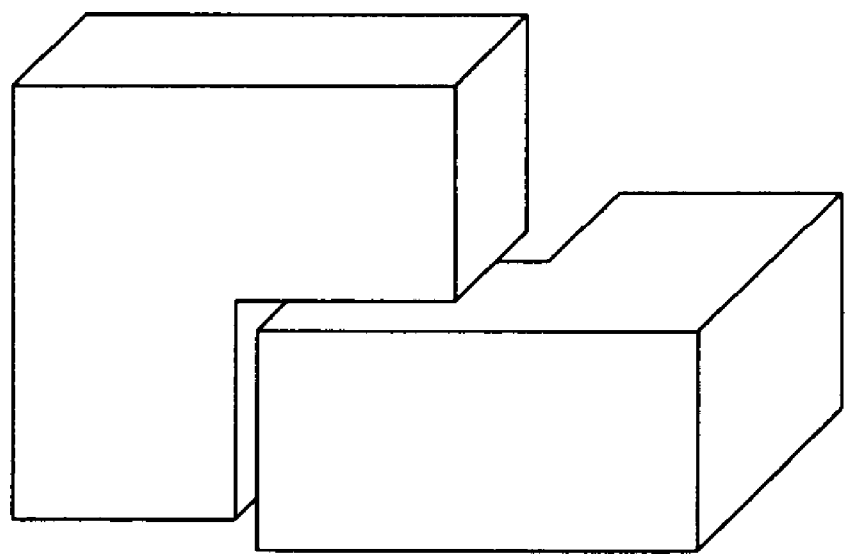

The various described shapes can also be described as a merging of imaginary cubes to make the described shape, or more generally a merging of rectangular prismatic shapes to make the desired shape. For example, the L is a merging of three imaginary cubes in the form Merging of four imaginary cubes gives a prismatic T; or a prismatic Z; or an out-of-plane Z. Finally, a merging of four imaginary cubes can give a corner piece. A merging of five cubes can give a cruciform prismatic shape. Shown in FIGS. 17A and 17B are some possible nesting patterns for L's. Nesting patterns could also be envisioned for the other described shapes.

Surface and/or Internal Geometric Features

Figure 18:
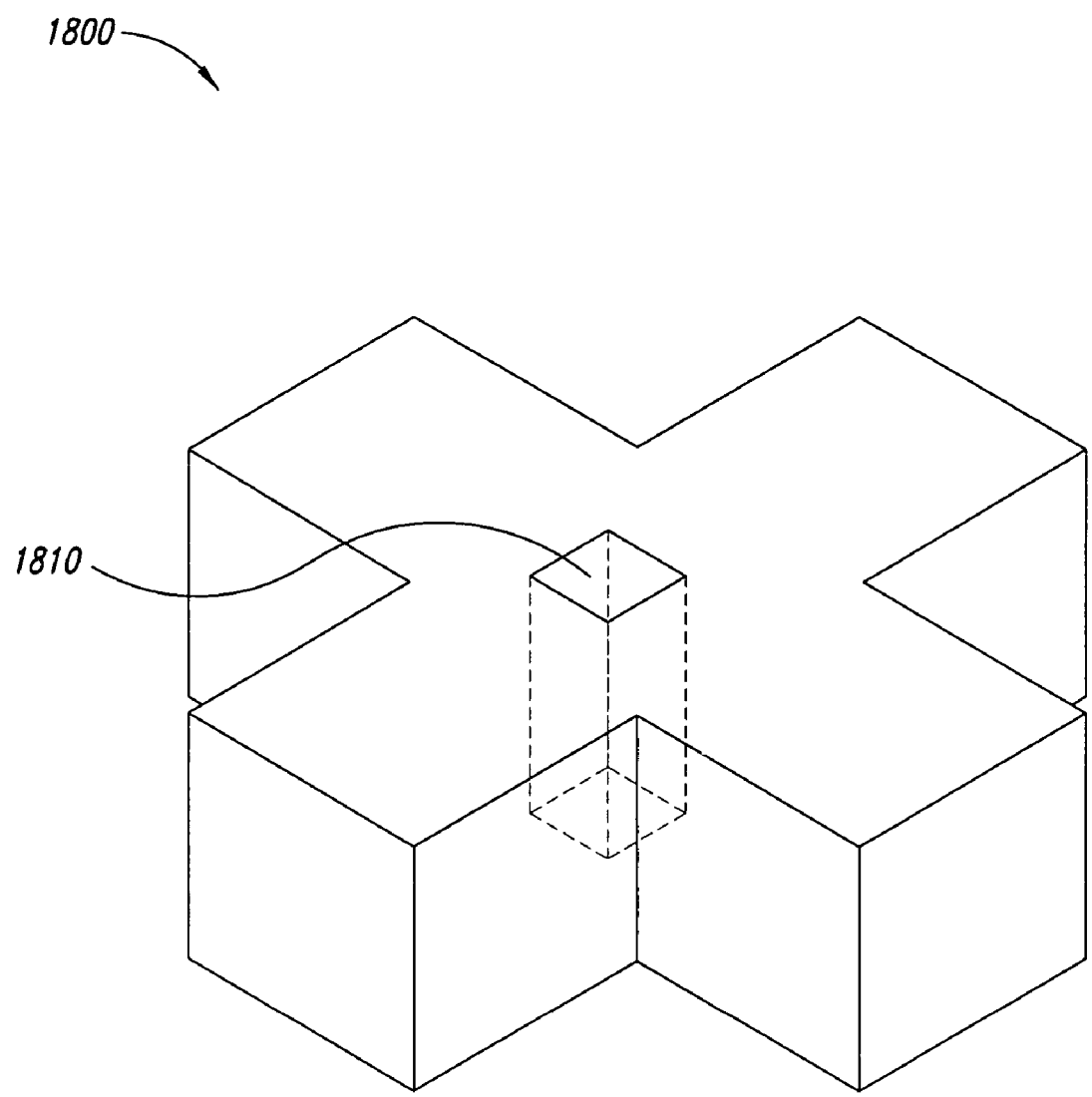
FIG. 18 illustrates a cruciform prismatic bone void filler piece containing a single hole through its central region in accordance with principles of the present invention.

The bone void filler pieces may also have other features. For example, the bone void filler pieces may have one or more holes through them. The holes may be of square cross-section, which is convenient for one of the manufacturing methods described herein, or in general any other cross-section. FIG. 18 illustrates a single hole 1810 that intersects the cruciform planar surface of a cruciform prismatic bone void filler piece 1800.

Figure 19:
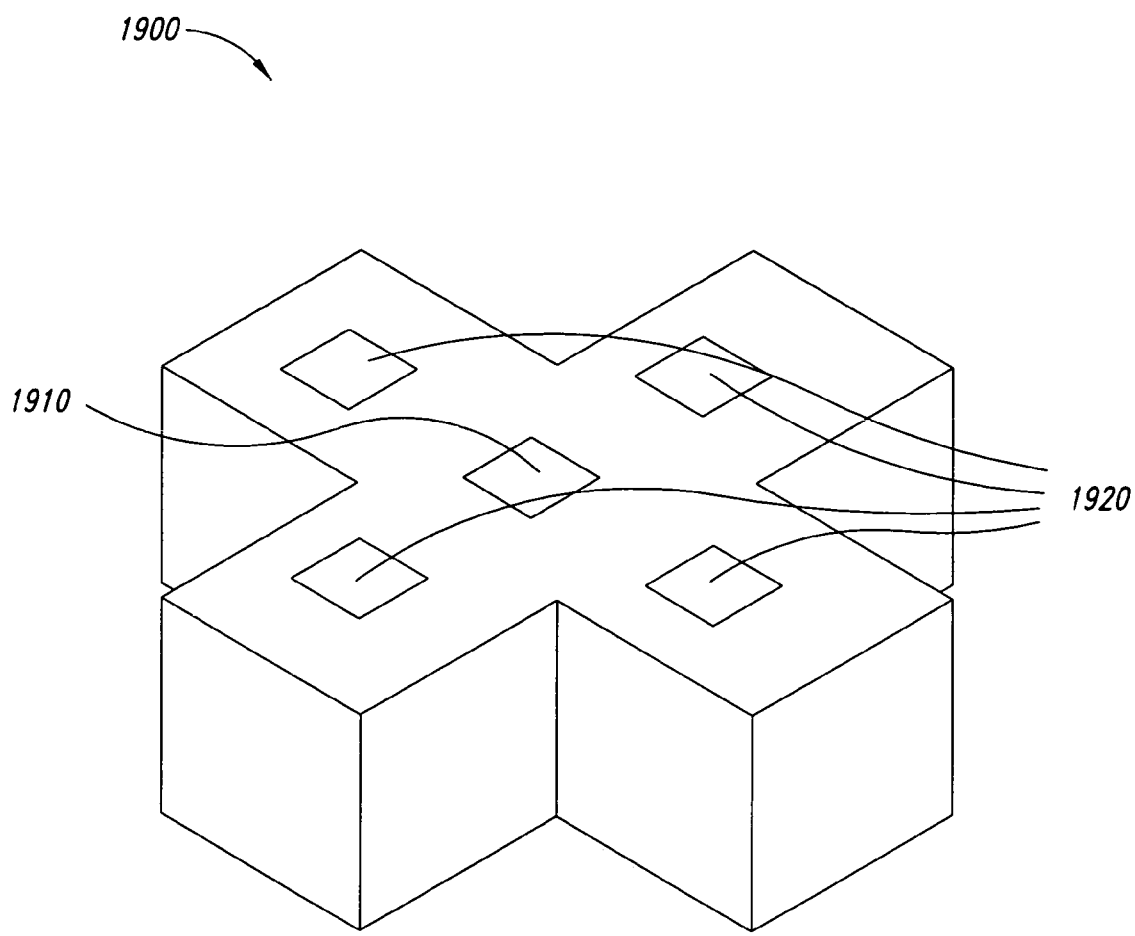
FIG. 19 illustrates a cruciform prismatic bone void filler piece with five holes through it in accordance with principles of the present invention.

FIG. 19 illustrates a cruciform prismatic bone void filler piece 1900 with five holes through the cruciform planar surface, i.e., one hole 1910 in the central region of the cruciform shape and one hole 1920 in each of the arms. (For clarity in this illustration, hidden lines of the holes are omitted.)

Figure 20:
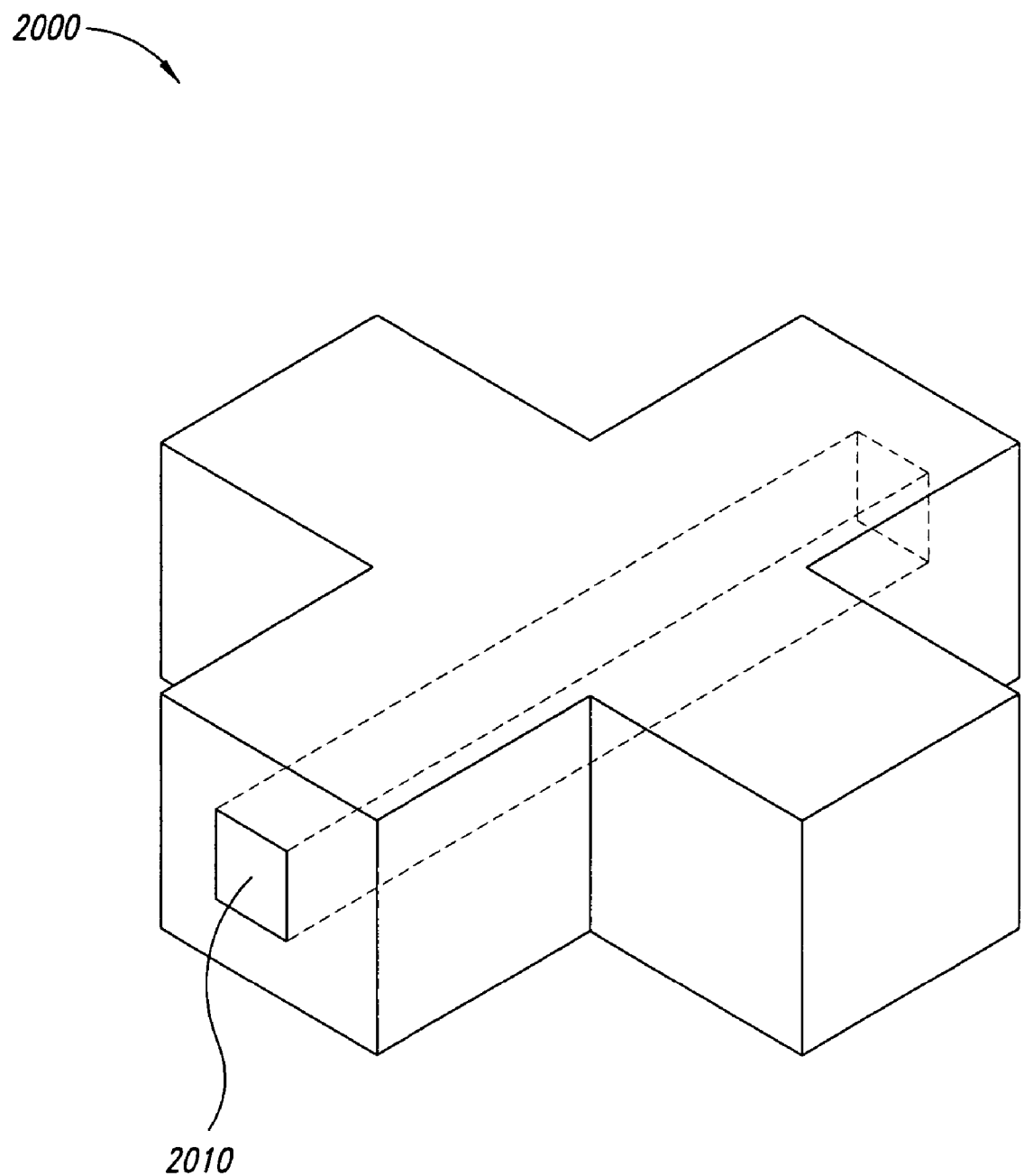
FIG. 20 illustrates a cruciform prismatic bone void filler piece with a hole through one of the arms in accordance with principles of the present invention.

FIG. 20 illustrates a cruciform prismatic bone void filler piece 2000 with a hole 2010 through one of the arms along the length of the arm, parallel to the cruciform planar surface. Alternatively, the bone void filler piece could also have a similar hole in the other arm. Multiple holes or even intersecting holes could be created if space permitted.

In general, it is possible that any of the shapes described herein could be made with one or more internal holes, either through-holes or blind holes, of any cross-section and any aspect ratio, and in any orientation and in any combination.

Yet another possibility is that any of the shapes described herein could be made with macroscopic surface indentations such as grooves or tire-treads. One example of a groove is a groove that goes around the perimeter of a cruciform prismatic bone void filler piece. For example, both cross-sectional dimensions of the groove could be in the range of from approximately 0.1 to approximately 0.5 of the prismatic dimension of the bone void filler piece.

Figure 21:
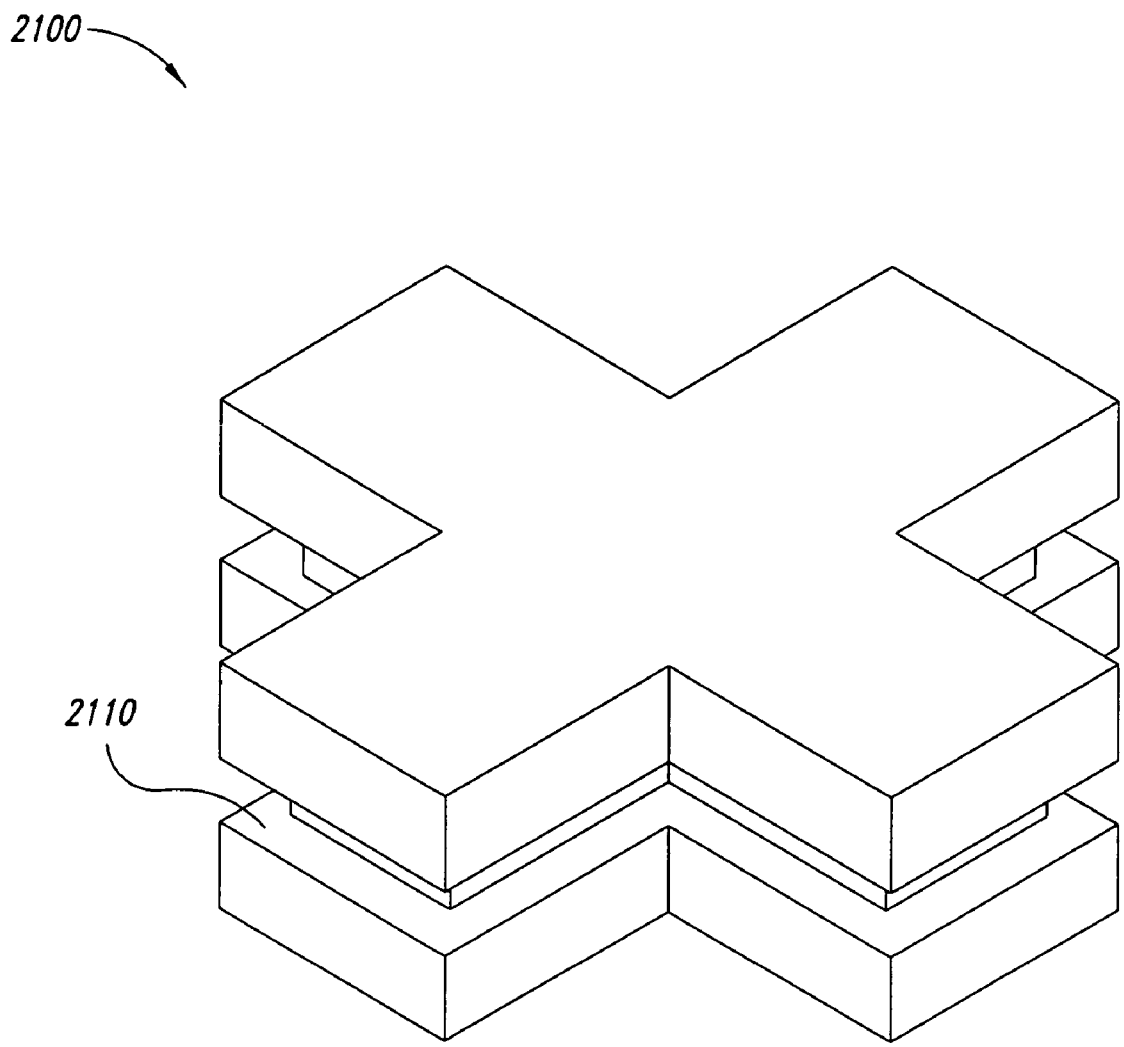
FIG. 21 shows a bone void filler piece which contains a groove embedded in one of the planar surfaces in accordance with principles of the present invention.
Figure 22:
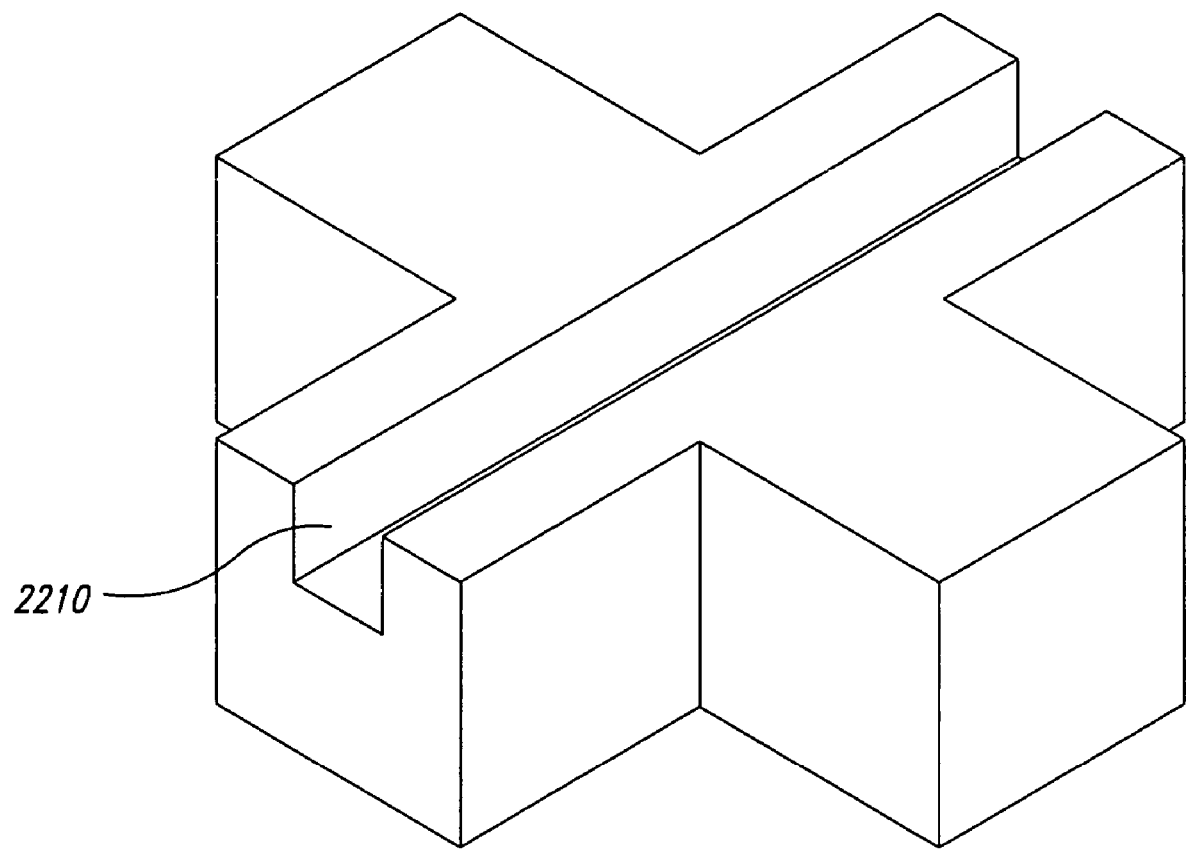
FIG. 22 shows a bone void filler piece with another such groove in accordance with principles of the present invention.

Another example of a groove is a groove 2110 which is embedded in one of the planar surfaces of the bone void filler piece 2100, which define a base of the prismatic shape, as shown in FIG. 21. Of course, additional such grooves could exist in the other arm, in the prismatic surface on the opposite side of the same bone void filler piece, etc. Such grooves or surface recesses could be put in any of the other disclosed shapes of bone void filler pieces, as well. The grooves 2210 or surface recesses could extend the full length of the face (as shown in FIG. 22) or could be less than the full length of the face.

It is possible that a bone void filler piece could have grooves in multiple surfaces in any combination. It is possible that a bone void filler piece could have both grooves and holes, in any combination.

Method of Manufacture

The invention also includes aspects of methods of manufacture of the described bone void filler. According to one aspect of the present invention, the method to manufacture the bone void filler pieces can include three-dimensional printing (3DP). 3DP provides the ability to precisely determine local geometric features and composition of a manufactured article, to an extent that is not possible with most other manufacturing methods. The method also may include a chemical reaction of precursor substances to form a desired ceramic substance such as tricalcium phosphate. The method also may include the use of a decomposable porogen mixed in with a starting powder. Any of these aspects of the method may be used separately or they may be used in any combination.

Figure 23:
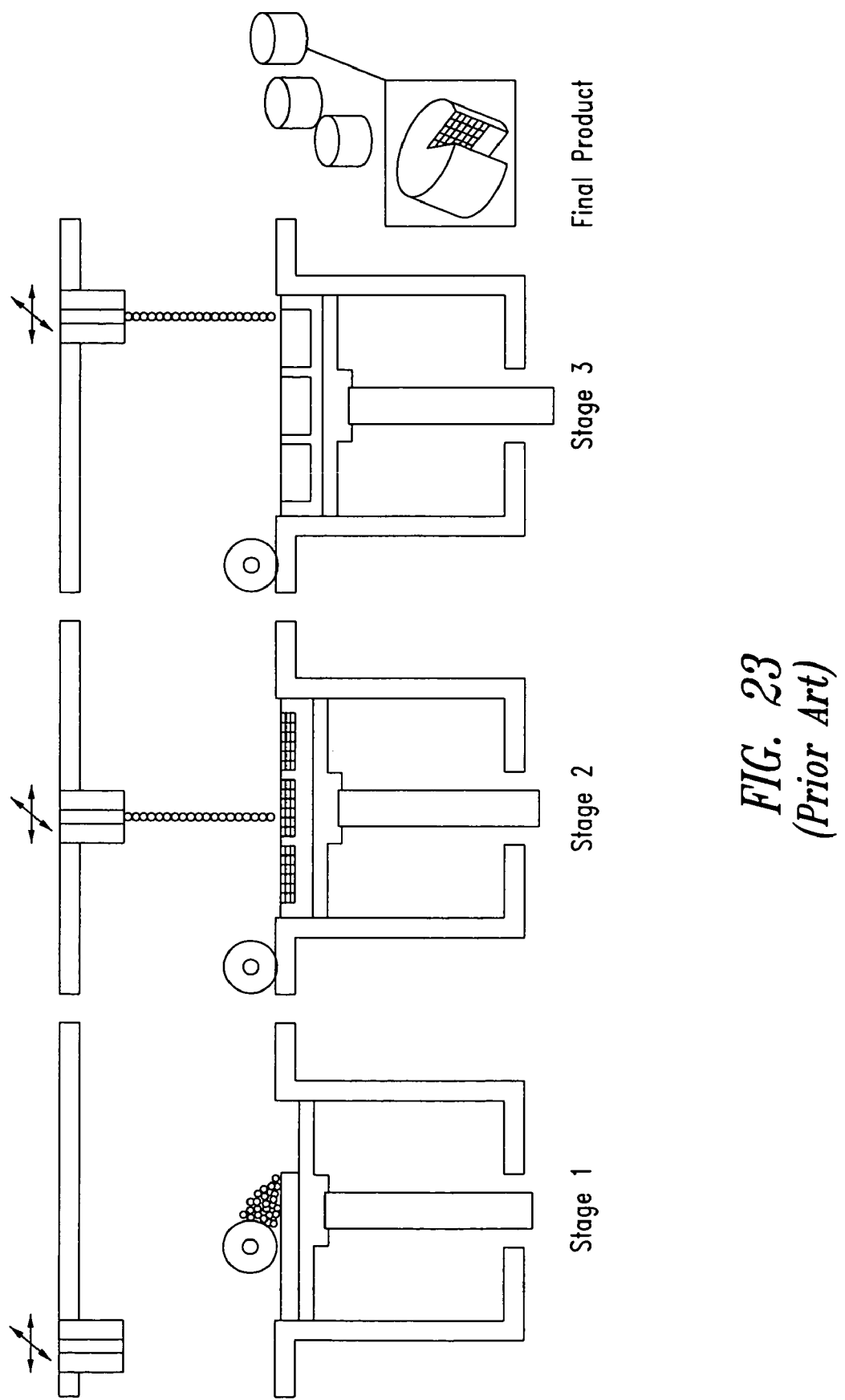
FIG. 23 illustrates a conventional three-dimensional printing process in accordance with the prior art.

Three-dimensional printing, illustrated in prior art FIG. 23, includes a set of steps that may be repeated as many times as are necessary to manufacture an article. At the beginning of the set of steps, powder may be deposited in the form of a layer. The powder may be deposited by roller spreading or by other means such as slurry deposition.

For the present invention, the powder may comprise both particles of ceramic or precursors of a ceramic, and particles of a porogen. The proportion of the porogen to the ceramic or ceramic precursors may be chosen so as to result in a finished product having a desired porosity. The sizes and size distribution of the particles of ceramic or ceramic precursors and the particles of the porogen may be chosen so as to determine the size and size distribution of the pores in the finished product. The ceramic may be tricalcium phosphate, and, in particular, may be beta tricalcium phosphate. The ceramic may be any other desired ceramic.

In one aspect of the present invention, the deposited powder may comprise particles of precursors of ceramic. Precursors may include hydroxyapatite and dicalcium phosphate. Additionally, precursors may include calcium pyrophosphate or other calcium-phosphorous compounds, as described elsewhere herein or in the incorporated references. The ceramic or precursor may in general include any member or members of the calcium phosphate family.

In another aspect of the invention, the deposited powder may comprise the desired ceramic. For example, the deposited ceramic may be tricalcium phosphate, and in particular, may be beta tricalcium phosphate. The ceramic may be any other desired ceramic or mixture of ceramics.

In another aspect of the invention, the deposited powder may include particles of a porogen; the porogen may be decomposable. The proportion of the porogen to the other particles in the deposited powder may be chosen so as to result in a finished product having a desired porosity. The sizes and size distribution of the other particles, which may include ceramic and/or precursors, and the particles of the porogen may be chosen so as to determine the size and size distribution of the pores in the finished product.

The porogen may be lactose, such as spray dried lactose, or another sugar, or in general, any substance which is capable of decomposing into gaseous decomposition products, at a temperature that is permissible for the materials already in the product at the time of decomposition. This may be done with the other particles comprising either the desired ceramic, or precursors, or both. This temperature may, for example, be below a sintering temperature of the ceramic powder.

The average size of the particles of the porogen may be larger than the average size of the particles of the rest of the powder, and may even be significantly larger such as by a factor of approximately five. For example, the size of the lactose particles may be on average approximately 120 to 150 micrometers while the size of the other particles may be on average approximately 10 micrometers. The proportion of decomposable porogen to other substances may be, for example, 0 to 50% by weight. It has been found that a powder containing a combination of porogen such as lactose and ceramic or precursor materials is easier to roller-spread in a three-dimensional printing process than a powder containing only ceramic or precursor material.

After the deposition of a powder layer, drops of a liquid may be deposited onto the powder layer to bind powder particles to each other and to other bound powder particles. At each powder layer, timing of drop deposition such as from a printhead may be coordinated, for example by software, with the motion of the printhead in two axes, to produce a desired pattern of deposited droplets. The term droplets can be understood to include not only spherical drops but also any of the various possible dispensed fluid shapes or structures as are known in the art.

A dispensing device suitable for dispensing small quantities of liquid drops, which may resemble an ink-jet printhead, may dispense the liquid. For example, the dispensing device could be a microvalve (The Lee Company, Essex, Conn.) or it could be a piezoelectric drop-on-demand printhead or a continuous-jet printhead or other type of printhead as is known in the art. The liquid may comprise a binding substance dissolved in a solvent, which may be water.

There are various orientations of the bone void filler piece within the build bed of a three-dimensional printing machine. If some surfaces of the bone void filler piece are substantially parallel to layers of the three-dimensional printing (3DP) process, those surfaces may achieve approximately isotropic roughness while other surfaces may have ridges corresponding to layers of the 3DP process. Alternatively, a bone void filler piece with ridges on substantially all of its surfaces could be achieved by manufacturing the bone void filler piece using three-dimensional printing and orienting the bone void filler piece in the 3DP build bed such that, in the position which the bone void filler piece is horizontal. For example, one of the principal axes of the bone void filler piece could be oriented at an angle of approximately 45 degrees to the vertical axis of the 3DP machine, which is the build direction of the 3DP process.

The binding substance may be capable of decomposing, into gaseous decomposition products, at a temperature that is permissible for the materials already in the product at the time of decomposition. The binding substance may, for example, be polyacrylic acid. In certain materials systems (such as demineralized bone matrix), the binder substance may be left in the finished product. In certain materials systems, such as polymers, the binder liquid may be a pure solvent.

After this liquid dispensing process is completed on one layer, another layer of powder may be spread and the liquid dispensing may be repeated, and so on until a complete three-dimensional object has been built. The printing pattern(s) in each printed layer may in general be different from the printing pattern(s) in other layers, with each printing pattern being chosen appropriately so as to form an appropriate portion of a desired article. During printing, the unbound powder supports the bound shape and the later deposited layers of powder. At the end of the printing process the powder particles that are unbound and untrapped may be removed, leaving only the shape that has been bound together.

After separation of the bound shape from unbound powder, the bound shape may be processed with a heat treatment suitable to accomplish any one or more or all of several purposes. (For certain powder materials such as polymer and demineralized bone matrix, heat treatment may be impermissible.) The heating may be performed so as to thermally decompose the decomposable porogen (if used) so that the porogen exits the bound shape in the form of gaseous decomposition products. A typical decomposable porogen may decompose at well under 400 C.

The heating may also be performed so as to thermally decompose the binder substance so that the binder substance also exits the bound shape in the form of gaseous decomposition products. A typical temperature for this purpose may be 400 C.

The formation of a desired final ceramic from precursors can involve a chemical reaction. For example, hydroxyapatite, which is $Ca_{10}(PO_4)_6(OH)_2$, plus dicalcium phosphate, which is $CaHPO_4$, yields tricalcium phosphate. Further details of chemical reaction among calcium-phosphorus compounds are given in commonly assigned U.S. patent application Ser. No. 10/122,129. This reaction may take place at elevated temperatures such as 1100 C or higher, depending on individual chemistry and time duration.

The following is an exemplary reaction as described above:

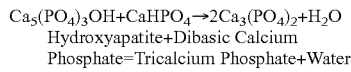

$Ca_5(PO_4)_3OH + CaHPO_4 \rightarrow 2Ca_3(PO_4)_2 + H_2O$
Hydroxyapatite+Dibasic Calcium Phosphate=Tricalcium Phosphate+Water Either if ceramic particles are used directly or if desired ceramic substances are formed from precursors, the heating may also be performed so as to partially sinter the ceramic particles together, thereby forming a porous structure of ceramic particles bound directly to other ceramic particles. A typical temperature and duration for this purpose, for members of the calcium phosphate family, may be 1100 to 1300 C for one to several hours depending on the ceramic. The heating may also be performed so as to cause reaction of precursors to form the desired final ceramic, if such materials are used.

The described heating may be performed in an oven whose atmosphere is ordinary atmospheric air, or can be performed in other special atmosphere if needed.

The method of the present invention can include the formation of a reaction product, such as a ceramic such as tricalcium phosphate, from precursors, regardless of whether three-dimensional printing is or is not used. The method of the present invention can include the use of a decomposable porogen, regardless of whether three-dimensional printing is or is not used. The method of the present invention can include the use of a decomposable binder substance, regardless of whether three-dimensional printing is or is not used.

Bone Void Filler Manufactured by Three-Dimensional Printing.

The invention also includes a bone void filler manufactured by three dimensional printing, in accordance with the method described above. The invention also includes a bone void filler manufactured by using a decomposable porogen together with reacting ceramic precursors to form a desired final ceramic.

Bone Void Filler Involving Molding

At least in some cases, the bone void filler of the present invention could also be manufactured by molding. The powder might be mixed with a binder substance or might simply be confined in a mold. It could be removed from the mold for the high-temperature processing or could be left in the mold if the mold were made of suitable materials. The process could include the use of a chemical reaction at elevated temperature to form tricalcium phosphate. The process could further include the use of a decomposable porogen.

The invention is further described but is in no way limited by the following non-limiting Examples.

Example 1

The bone void filler (BVF) of the instant invention is comprised of many medium sized pores with a lower frequency of large void spaces (See FIG. 8). The bone void filler is sponge-like with many medium size pores. This is in contrast to some granular fillers (i.e., Vitoss) has a porous web-like network that have many large void spaces (See FIG. 9).

The frequency of pores and pore distribution is evident in FIG. 36. Using mercury porosimetry the pore distribution was estimated. The bone void filler scaffolds of the instant invention (lower curve) have a high frequency of small pores with majority distribution falling between 5-80 microns. The prior art bone void filler scaffolds (higher curve) has a bimodal distribution with peaks at less than 10 microns and at 250 microns.

From SEM images such as shown in FIGS. 8 and 9, the pore area, pore diameter and porosity can also be estimated.

| | | Pore Area and Porosity | | |
|---|---|---|---|---|
| Device | Total | Mean | Min* | Max |
| | | Pore Area ($\mu m^2$) | | |
| BVF | $7.2 \times 10^5 \pm 6.6 \times 10^4$ | $3000 \pm 1200$ | 40 | $3.5 \times 10^5 \pm 2.1 \times 10^5$ |
| | | Pore Diameter ($\mu m$) | | |
| BVF | NA | $60 \pm 12$ | 7 | $640 \pm 220$ |
| | Device | | Porosity (%) | |
| | BVF | | $59 \pm 5.3$ | |

Pore area ($\mu m^2$) was estimated using SEM images (n = 30) and Image Pro ® software. Data are Ave ± Stdev except for minimum*. The pore diameter was estimated from the pore area by assuming circular shaped pores (equation 2). For the pore area and pore diameter, the mean and maximum ranges were estimated.
*All finite (<40 $\mu m^2$) pore structures were excluded from the analysis and therefore the minimum pore area is represented by 40 $\mu m^2$ and the pore diameter by 7 $\mu m$.

The porosity was estimated using the total pore area (μm²) shown in Table 1 (n=30) in conjunction with equation 1. The pore diameter was estimated from the pore area by assuming circular shaped pores (equation 2). The porosity for Vitoss™ was significantly greater than the bone void filler of the present invention. Comparisons were made using a students t-test, p<0.05.

True Density

True density or absolute density is obtained when the measured volume excludes the pores within the sample material. Using a mortar and pestle, the bone void filler of the present invention was crushed and a 3.5 to 5.5 gram sample loaded into a pycnometer (Accupyc™ 1330 Pycnometer, Micromeritics, Inc.; Norcross; Ga.) to determine the true density.

Bulk Packing Density

The bulk density gives an estimate of the implant material packing characteristics and is dependent on size, shape and porosity. A 10 mL volume of each device was measured using a 50 mL graduated cylinder (No. 20022, Kimble Glass Inc.; Vineland, N.J.). The cylinder was passively filled to the 10 mL mark; only light tapping was used to settle the contents. The mass of the contents was measured, and the packing density of each device determined (Equation 1).

| Parameter | BVF |
|---|---|
| True Density (g/mL) | 1.530 ± 0.001 |
| Bulk Packing Density (g/mL) | 0.53 ± 0.02 |
| Packing Porosity (%) | 65.7 ± 1.4 |

The true density and packing density were measured for BVF Data are Ave±Stdev for N=5 samples. The packed porosity was estimated based on equation 2. Statistically significant differences (p<0.05), using a t-test assuming equal variances, were identified for the packing density and packing porosity.

Example 2

Bone void filler pieces as already described were manufactured by three-dimensional printing. The powder that was spread was a mixture of spray-dried lactose (Pharmatose, The Netherlands) as a porogen and a ceramic powder.

The ceramic powder, which comprised precursors to the desired ceramic, was a mixture of hydroxyapatite and dicalcium phosphate and other calcium phosphates. It had the composition approximately 79.9% hydroxyapatite, 20.1% dicalcium phosphate (by weight). It was obtained from Cosmocel S. A., Monterrey, Nuevo Leon, Mexico. The mean powder particle size was between 5 and 8 micrometers, with the majority being below 10 micrometers.

The proportion of porogen to ceramic was 60% ceramic and 40% porogen by weight, although this can be varied. It has been found that this ceramic-plus-lactose powder was easier to spread with a roller than was the same powder without lactose.

Layers were spread in a layer thickness of approximately 400 micrometers.

The binder liquid was an aqueous solution of polyacrylic acid.

| 1037 | Acumer 1510 (25 wt % polyacrylic acid solution), | 22.87 |

-continued

| 1038 | Glycerin, USP | 0.41 |
|---|---|---|
| 1006 | Water, purified, USP | 76.52 |
| 1054 | Methylparaben, NF | 0.18 |
| 1055 | Propylparaben, NF | 0.02 |

The binder liquid was dispensed through microvalves (Lee Corporation, Essex, Conn.) with an orifice of diameter 0.004 inch (102 micrometers).

After harvesting of the bound shapes, the bound shapes were processed through a thermal cycle which was: room temperature up to 400 deg C. at 10 deg C./min (hold 1 hr); ramp to 1200 deg C. at 5 deg C./min (no hold) and ramp up to 1245 deg C. at 1 deg C./min (hold for 2 hours). Various other thermal cycles would also be possible.

The bone void filler pieces were manufactured to dimensions of approximately an overall arm dimension of 5 mm and a prismatic height of 3 mm, as shown in the illustration.

It was found that the overall packed density of the bone void filler of the present invention was noticeably larger than that of the previously described prior art. The difference was greatest in what is termed the Bulk Packing Density. This quantity is the overall material density of a plurality of crosses (present invention) or morsels (Vitoss) poured into a bone void or occupying a jar, compared to the density of the same material as a pure solid, and takes into account both the internal porosity of individual pieces and the manner in which the pieces geometrically nest or stack.

In terms of this descriptor, the difference between the two products is more than a factor of two, and is statistically significant. The increased density and other characteristics of the instant invention promote more favorable bone ingrowth for the bone void filler of the present invention. For example, the increased density equates to more ceramic material in the defect site at implantation. This provides a longer time period, wherein a structure is still in place, for bone ingrowth and remodeling to occur.

Figure 24A:
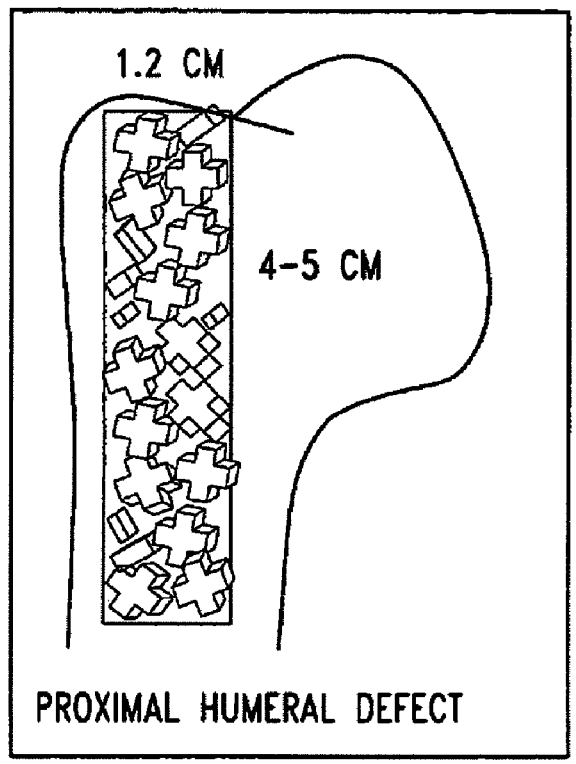
FIG. 24A is a schematic illustration of the implanted bone void filler in accordance with principles of the present invention.
Figure 24B:
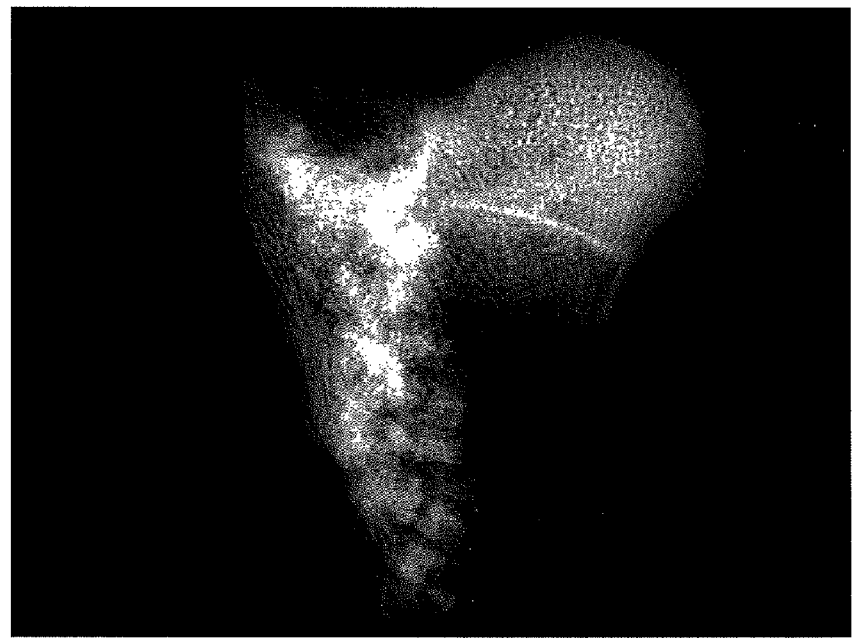
FIG. 24B is an X-ray of a bone filled with bone void filler pieces in accordance with principles of the present invention.

The resulting bone void filler pieces of the present invention were then implanted in voids which were created in the humerus of dogs, as shown in the following pictures. They were then allowed to grow for various periods of time, at which point the animals were sacrificed and histology of the resulting bone was performed. FIG. 24A illustrate a schematic illustration of the implanted bone void filler of the present invention. FIG. 25 is an X-ray of the end of the bone, where a void in the bone has been filled with bone void filler pieces of the present invention, and some healing has been allowed to take place.

Figure 25C:
FIGS. 25A-D are histology pictures showing cruciform bone void filler pieces of the present invention after implantation and growth in an animal in accordance with principles of the present invention.
Figure 25A:
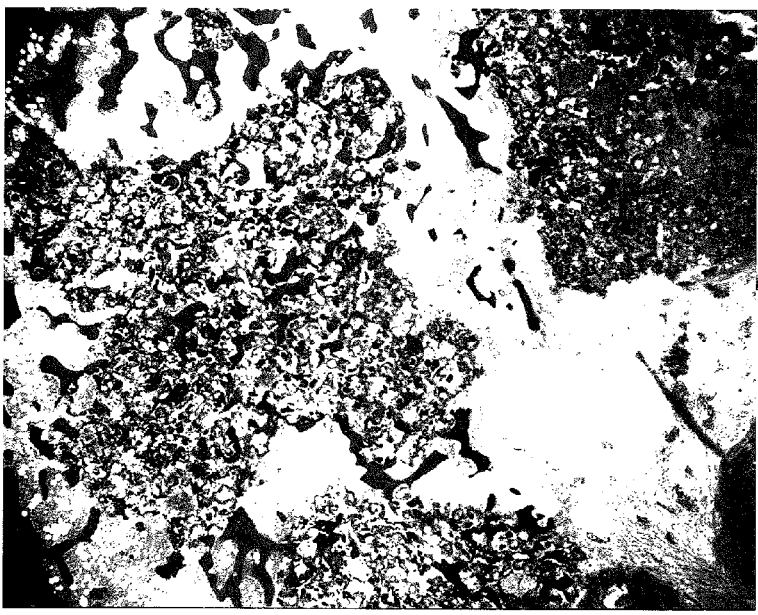
Figure 25B:
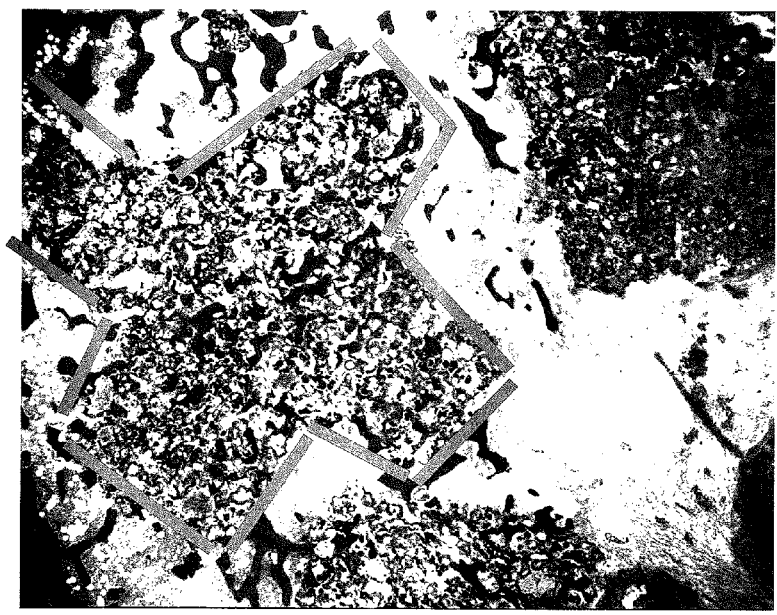
Figure 25D:
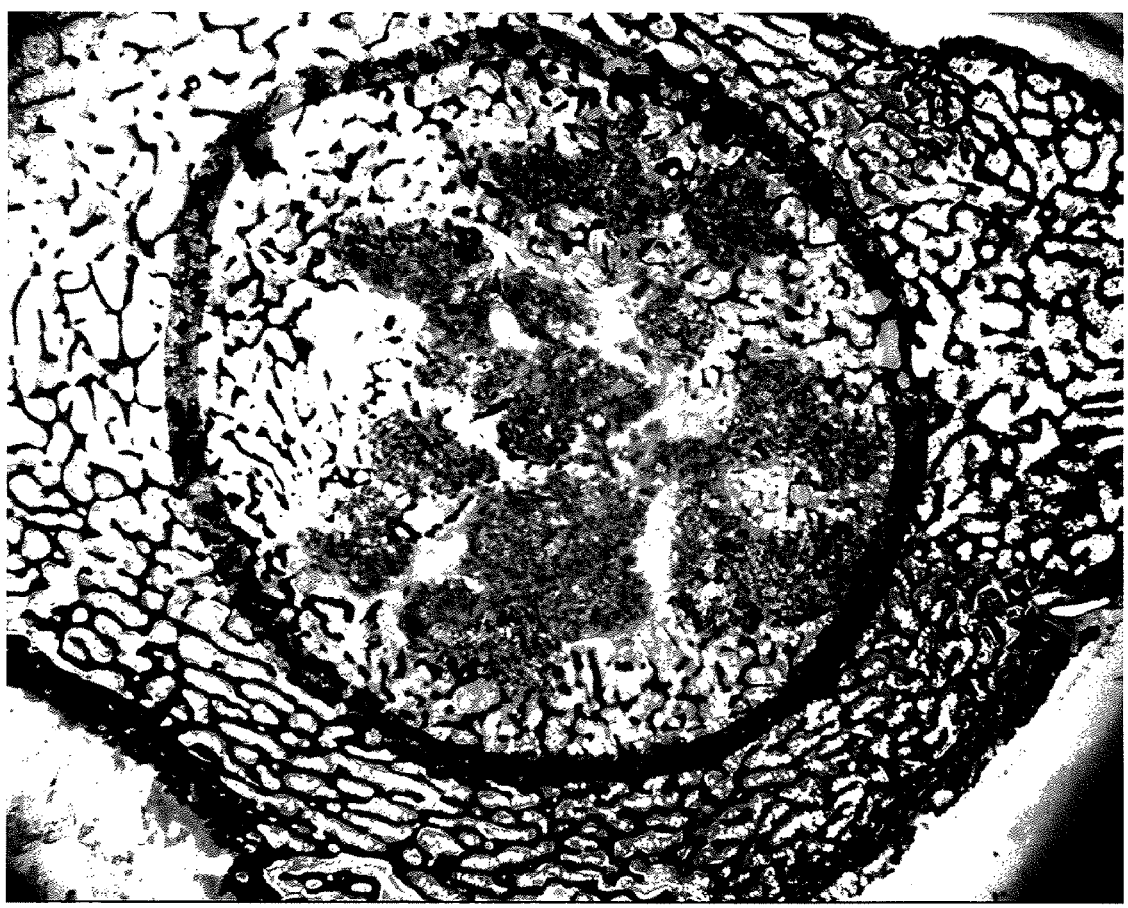

FIGS. 25A-D are histology pictures showing cruciform bone void filler pieces of the present invention, or remnants thereof, distinguishable within bone tissue that has already grown in as part of the processing of healing the void. FIGS. 25A and 25B are the same pictures, except that in 25B, the outline of one original cruciform bone void filler piece is marked for reference. FIG. 25C is a lower magnification view showing the entire end of the bone into which the bone void filler was placed, and showing all of the bone void filler pieces which occupy that cross-section of the void in the bone.

The bone filler material, due to the higher bulk packing density, undergoes more controlled resorption, and therefore provides a stable structure (i.e., foundation) for the duration of complete healing (i.e. a period defined up to 1 year post implantation). Particularly at the middle time periods in this study, more of the bone void filler of the current invention remains at the site, in comparison to the situation for prior art bone void fillers, for example, Vitoss.

In general, a problem in the past has been that tricalcium phosphate, which is the principal resorbable form of calcium phosphate, resorbs somewhat too quickly in comparison with the rate at which natural bone can take its place. If the rate of resorption is undesirably quick, the resorbed material is replaced by some form of tissue but not necessarily by high quality bone. It is believed that the more extended existence of the current bone void filler is better suited to the rate of replacement by natural bone, and this enables high quality natural bone tissue to grow in place of the bone void filler. The presence of more ceramic material in the defect site does not, however, imply slower resorption rates of the bone filler or less potential bone ingrowth into the defect site.

As shown in the table below, in comparison to bone fillers with higher porosities and lower bulk packing densities (i.e. Vitoss), the bone void filler of the present invention has both higher amount of filler remaining and higher amount of new bone growth. This is believed to be associated with the improved mechanical strengths and stiffnesses that were measured with the product of the present invention.

| Percent Residual Material within Defect Site | | | |
|---|---|---|---|
| Percent New Bone | | Percent Residual Material | |
| Week | TheriLok ™ | vs. Vitoss ™ | TheriLok ™ | vs. Vitoss ™ |
| 12 | 18.9 ± 4.6 | 14.9 ± 4.6 | 27.6 ± 5.3 | 13.2 ± 4.5 |
| 24 | 20.4 ± 2.2 | 18.9 ± 1.6 | 16.6 ± 4.3 | 3.9 ± 3.3 |
| 52 | 22.1 ± 3.7 | 19.5 ± 2.1 | 6.5 ± 3.7 | 3.2 ± 2.5 |

The percent new bone growth was determined using a Merz grid. No significant differences ($\alpha = 0.05$) were observed within any of the implant comparisons at any measured timepoint. The percent residual implant material was determined using the point counting method with a Merz grid. At Week 12 and 24, TheriLok ™ (the BVF of the current invention) had significantly more residual implant material than Vitoss ™. This was expected due to differences in structure and packing densities of the two devices, which can impact the rate of material resorption. By Week 52, there were no differences in residual implant material between TheriLok ™ and Vitoss ™. Note that at 24 weeks, majority of Vitoss has resorbed, leaving no structure for subsequent healing and remodeling to occur.

The bone filler, due to the higher bulk packing densities, macro shape and extent of bone ingrowth, lends to a more mechanically stable bone-composite than typical granular bone fillers. This relates to structure function relationships, wherein the bone filler provides structure for an appropriate healing period and the functional outcome is the strength of the healed tissue—this was evident in testing the implants from the animal study mentioned previously.

| Mechanical Testing Data | | | |
|---|---|---|---|
| Mechanical | Test Area | | |
| Parameter | TheriLok ™ | Vitoss ™ | Native Bone |
| Stiffness (N/mm) | 1418 ± 907 | 1234 ± 711 | 2447 ± 1984 |
| Yield Force (N) | 663 ± 217 | 389 ± 174 | 757 ± 241 |
| Failure Force (N) | 786 ± 191 | 532 ± 121 | 804 ± 128 |

N = 6 for each test area. The Stiffness (elastic modulus), indicates the test material's ability to resist deformation under a load. Yield Force shows the load, or stress, at which the mechanical properties began to degrade and the stiffness of the test material was no longer linear. The Failure Force indicates the load that resulted in the fracture, or failure, of the test material. TheriLok was significantly higher than Vitoss in Yield and Failure force and similar to native bone in those categories.

Aggregate Aspects

The invention also includes an aggregate of bone void filler pieces that includes a variety of pieces having more than one of the shapes described herein. The aggregate can further include cubical or other shape bone void filler pieces in addition to including pieces that have one or more of the shapes described herein. It is also possible that not all of the pieces in an aggregate of bone void filler pieces need to have the same size scale. The aggregate could comprise a first group of bone void filler pieces having a first shape and a first size scale, and a second group of bone void filler pieces which has a second size scale and has either the same shape as the first group or a shape which is different from the shape of the first group.

The invention includes the use of particles of demineralized bone matrix together with any of the described bone void filler pieces. The particles of demineralized bone matrix may have an overall dimension in the size range of approximately 100 micrometers to approximately 900 micrometers, and more preferably an approximate size of 125 micrometers. The particles of demineralized bone may be packages together with the bone void filler pieces in a single container. Alternatively, the particles of demineralized bone may be packages in a container that is separate from the container holding the bone void filler pieces.

Material Composition and Properties

The bone void filler pieces may be made of particles of a matrix material that are partially joined directly to each other. The bone void filler pieces may be porous, having a porosity and a pore size distribution. One possible set of porosity and pore size distribution is described in "Bone void filler and method of manufacture," U.S. Ser. No. 60/466,884, as having a peak in the pore size distribution at approximately 60 micrometers.

Another possible porosity and pore size distribution is described in U.S. Ser. No. 10/122,129, as having a peak in the pore size distribution at approximately 8 to 20 micrometers. Typical porosities in either of these cases may be in the range from approximately 40% to approximately 70%. For demineralized bone matrix and polymer, the pore sizes may be larger, such as in the tens or hundreds of microns. These are not exact requirements, however.

The bone void filler pieces may be made of a material and a geometry that are suitable to promote wicking of bodily fluids into the bone void filler pieces. Wicking of bodily fluids may be advantageous in promoting ingrowth of natural bone. For example, the porosity and pore size described herein are suitable to promote wicking of bodily fluids that are not extremely different from water in their physical properties.

The bone void filler pieces may also be of a hardness such that they can easily be crushed if necessary.

The bone void filler pieces may be made of synthetic material such as ceramic, such as members of the calcium phosphate family. Specifically, the bone void filler pieces may be made of or may comprise tricalcium phosphate, which is biodegradable. The tricalcium phosphate may be of a crystal structure that is either alpha tricalcium phosphate or beta tricalcium phosphate or both, in any proportion. For example, the tricalcium phosphate may comprise approximately 80% beta tricalcium phosphate and approximately 20% alpha tricalcium phosphate.

Hydroxyapatite is another suitable member of the calcium phosphate family, which is nonresorbable. Yet another possibility is that the bone void filler pieces could be made at least partially of demineralized bone matrix, such as by having particles of demineralized bone matrix joined to each other by a binder substance. Yet another possibility is that the bone void filler pieces may comprise one or more polymers such as a biodegradable polymer.

The bone void filler pieces may further comprise any of various bioactive materials, such as are described in U.S. Ser. No. 10/122,129. The bone void filler pieces may further comprise a radio opaque marker, which may be resorbable. The bone void filler pieces may be sterile and may be packaged so as to maintain sterility.

Packaging, Dispenser

The bone void filler of the present invention may be contained or packaged in a container or dispenser that is suitable to deposit the bone void filler pieces into a surgical site. A container could be as simple as a jar. A container may be a syringe type dispenser in which a piston is slidably positioned inside a cylinder suitably to push the bone void filler pieces out of the cylinder.

Figure 26:
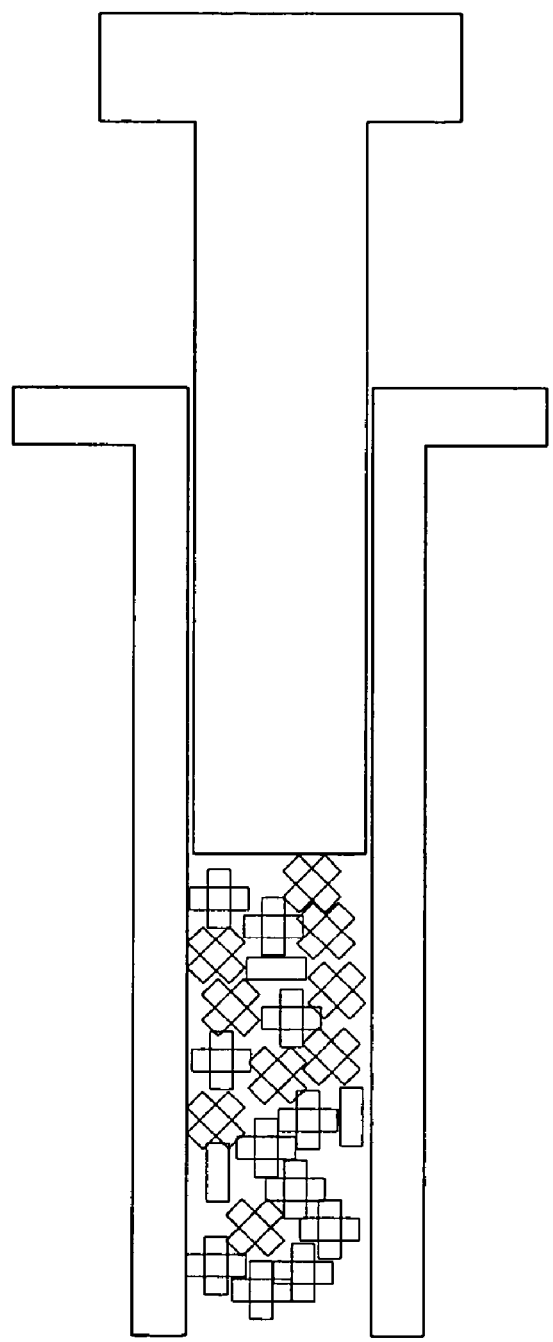
FIG. 26 illustrates dispenser may have an end opening which is large enough for an aggregate of bone void filler pieces to pass through in accordance with principles of the present invention.

As illustrated in FIG. 26, one possible form of dispenser is that the dispenser may have an end opening which is large enough for an aggregate of the bone void filler pieces, which may be in random orientation, to pass through. The piston-cylinder portion of this device may have a cross-sectional area, and the discharge end of this device may have an orifice area that is equal to or almost as large as the piston-cylinder cross-sectional area. This is illustrated in FIG. 26 with the two cross-sectional areas being equal to each other. The bone void filler pieces are shown inside this device having essentially random orientation with respect to each other.

Figure 27:
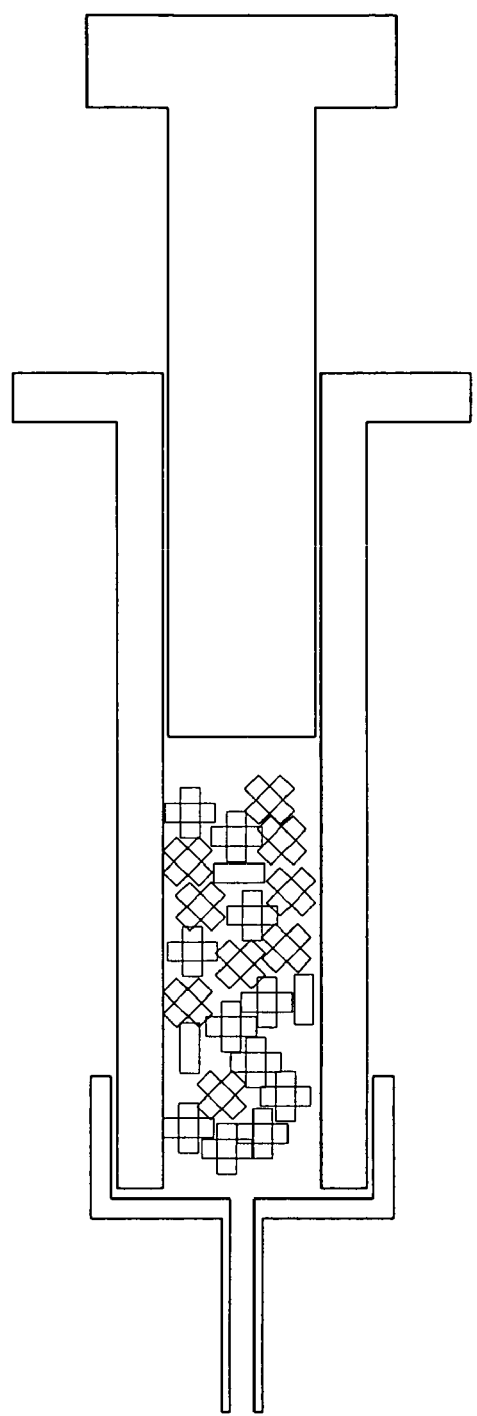
FIG. 27 illustrates a syringe ready to aspirate bone marrow or blood into the chamber of the syringe in accordance with principles of the present invention.
Figure 28:
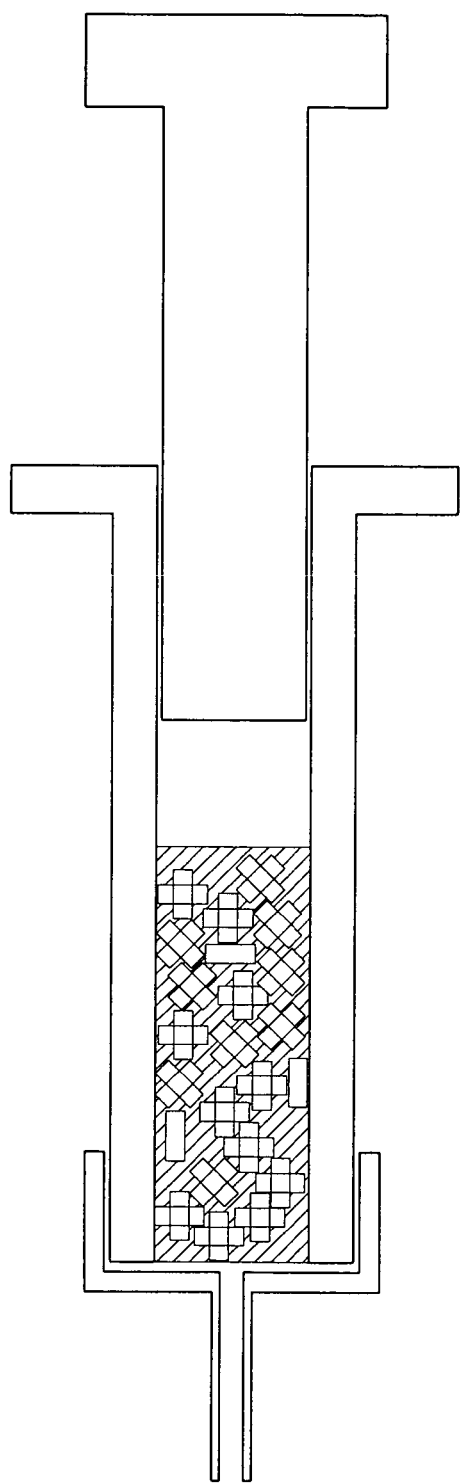
FIG. 28 illustrates the syringe after aspiration of blood or but prior to ejection of the bone void pieces in accordance with principles of the present invention.
Figure 29:
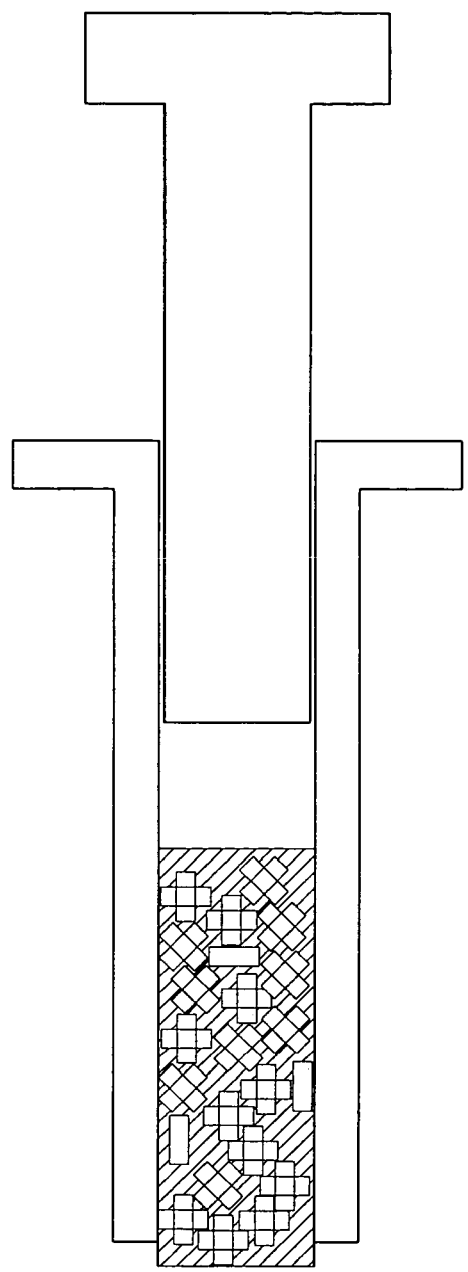
FIG. 29 illustrates the end cap portion of the syringe having been removed in accordance with principles of the present invention.
Figure 30:
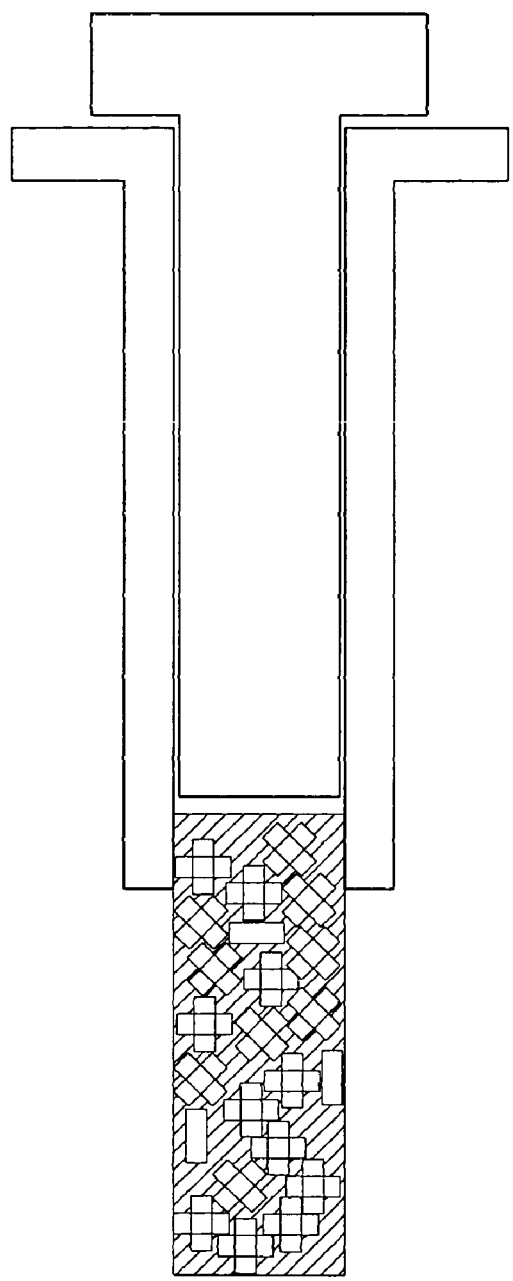
FIG. 30 illustrates the bone void filler pieces, having been soaked in blood or marrow, being ejected into a wound site (not shown) in accordance with principles of the present invention.

FIG. 27 illustrates a syringe with a dispenser tip in an initial state ready to aspirate bone marrow or blood into the chamber of the syringe. FIG. 28 illustrates the dispenser having aspirated blood or marrow to soak the bone void filler pieces but prior to ejection of the bone void pieces into the wound site. FIG. 29 illustrates the end cap portion containing the dispenser tip being removed in order to provide a wide mouth outlet for ejection of the bone void filler pieces. FIG. 30 illustrates the bone void filler pieces, having been soaked in blood or marrow, being ejected into a wound site (not shown).

Figure 31:
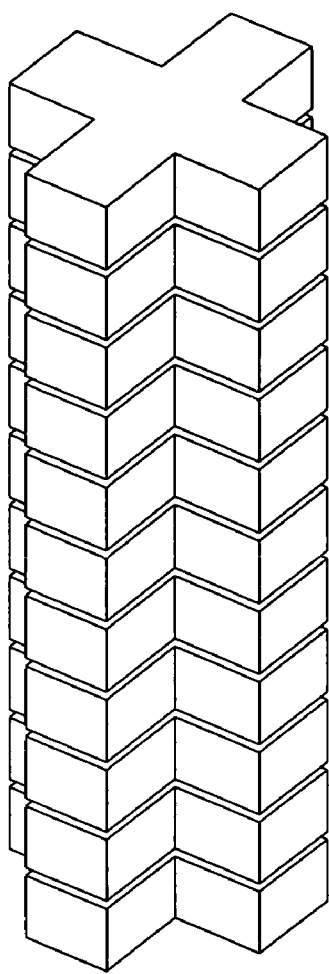
FIG. 31 shows cruciform bone void filler pieces stacked with corresponding prismatic surfaces parallel to each other and with the pieces angularly aligned with each other in accordance with principles of the present invention.
Figure 32:
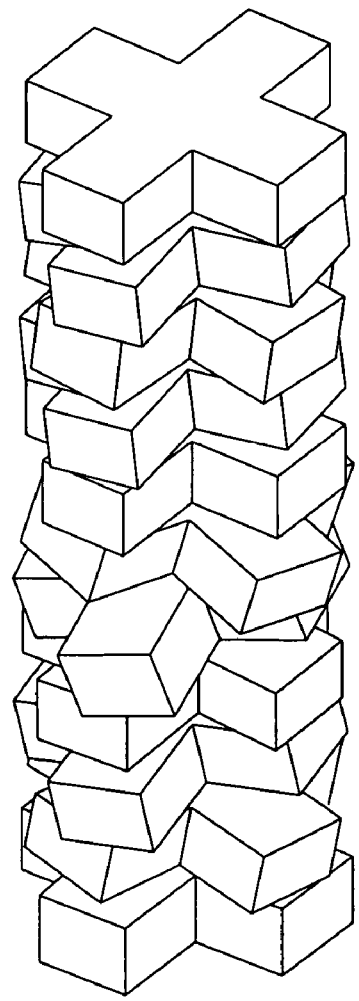
FIG. 32 shows cruciform bone void filler pieces stacked with corresponding prismatic surfaces parallel with each other and with the pieces having random angular orientation with respect to each other in accordance with principles of the present invention.

Another possibility is that the dispenser may have the bone void filler pieces stored inside it in a known orientation. For bone void filler pieces of the present invention, which are prismatic, this may comprise storing the pieces with prismatic surfaces facing prismatic surfaces of adjacent pieces. (Prismatic surfaces of a shape would be considered to be surfaces that are substantially parallel to each other and are connected by the extruded surface(s) that form the body of the prismatic shape.) For cruciform-shaped bone void filler pieces, this could comprise cruciform surfaces touching other cruciform surfaces in either of two ways, as illustrated in the following Figures. FIG. 31 shows the cruciform pieces stacked with corresponding prismatic surfaces parallel to each other and with the pieces angularly aligned with each other, and FIG. 32 shows the cruciform pieces stacked with corresponding prismatic surfaces parallel with each other and with the pieces having random angular alignment with each other.

Figure 33A:
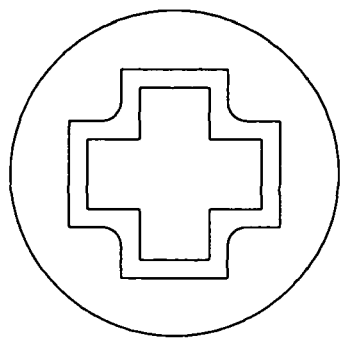
FIGS. 33A and 33B illustrate one embodiment of a dispenser for the present invention that allows aspiration of bone marrow or blood into the stacked bone void filler dispenser, and subsequent dispensing of product in accordance with principles of the present invention.
Figure 33B:
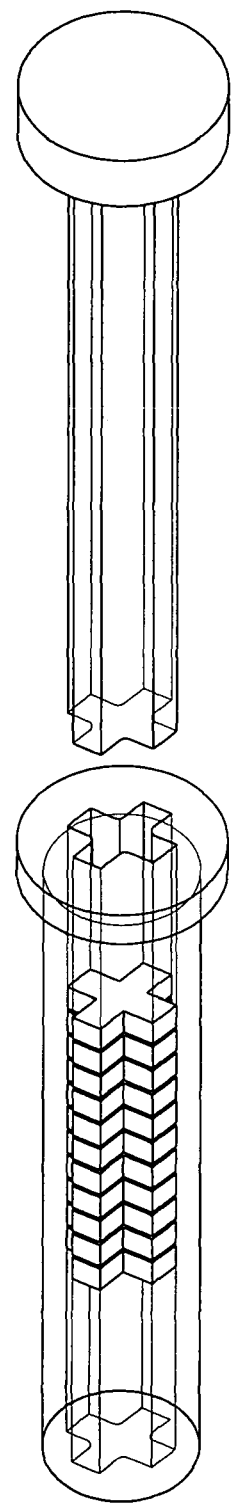
Figure 34:
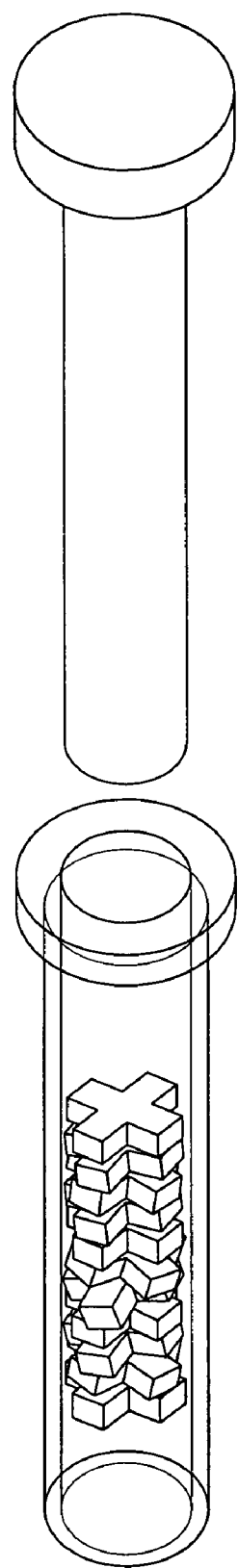
FIG. 34 illustrates a syringe that does not have angularly unique features in the syringe for aligning the bone void pieces in accordance with principles of the present invention.
Figure 35:
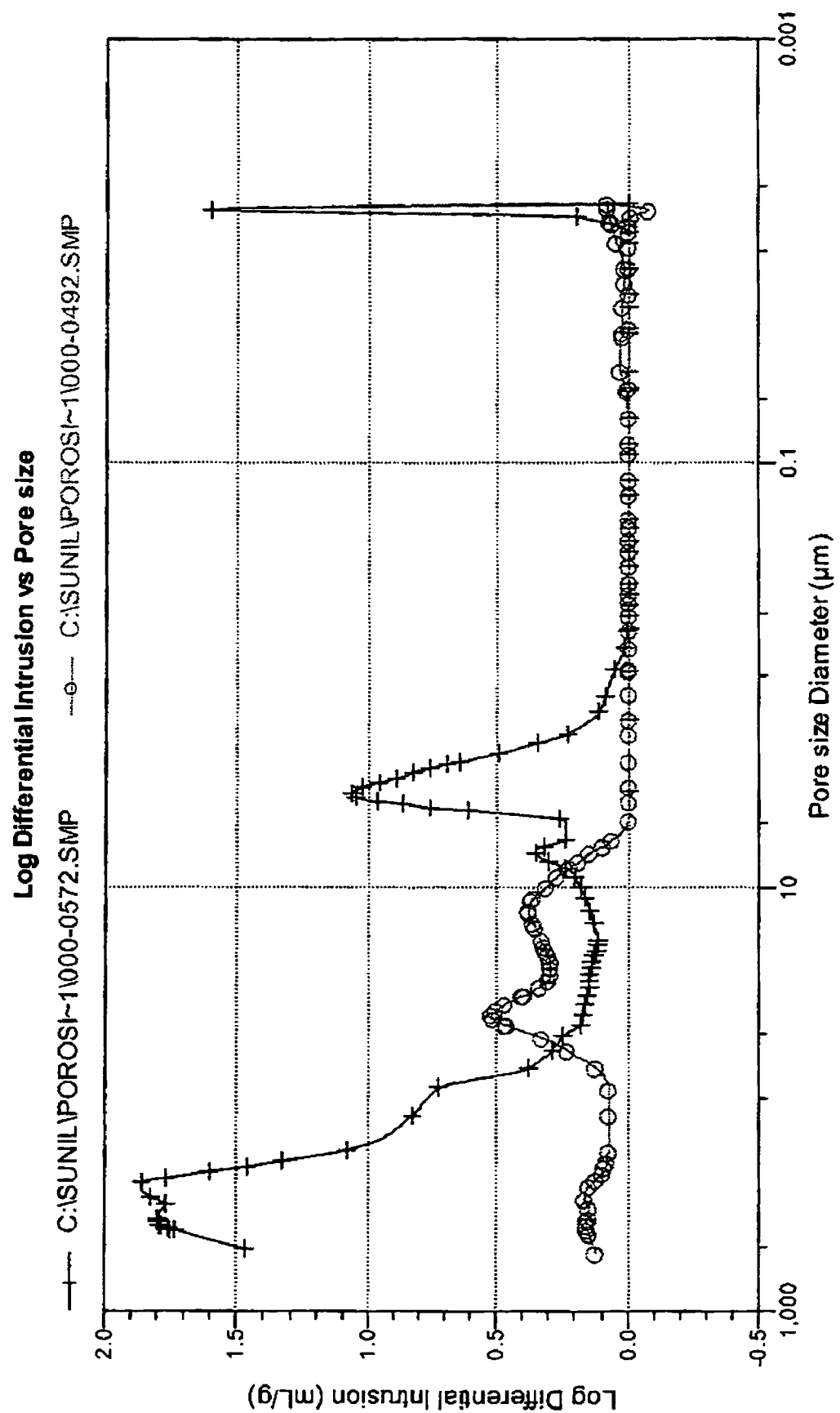
FIG. 35 is a graph of Intrusion in mL/g versus Pore Size comparing the current invention to a prior art invention in accordance with principles of the present invention.

FIGS. 33A and 33B illustrate one embodiment of a dispenser for the present invention that allows aspiration of bone marrow or blood into the stacked bone void filler dispenser, and subsequent dispensing of product. One useful thing about this sort of arrangement is that there would not be much need to remove a front-piece from the syringe, because the overall dispensing orifice would only be approximately the cross-sectional dimensions of one cruciform piece. You would be able to aspirate blood/marrow into that cross-sectional dimension, and then dispense the entire stack of cruciforms through that same cross-sectional dimension. One advantage of the stacked dispenser is that it could be small enough to stick into a minimally invasive surgery incision rather easily. FIG. 34 illustrates a syringe that does not have angularly unique features in the syringe for aligning the bone void pieces.

Method of Use

The bone void filler pieces can be used by basically pouring an aggregate comprising a plurality of bone void filler pieces into a bone void. The bone void may exist or be created for any reason, including, trauma, cancer, harvesting of a bone donation, etc. The bone void filler pieces disclosed herein may be used as filler material to occupy the interior of a spinal cage. It is possible that the dispenser, particularly a piston-cylinder type dispenser that stores the bone void filler pieces in a stack, may be sufficiently narrow to pass through a portal incision in minimally invasive surgery.

The method of installation may include soaking the filler piece in blood, platelet rich plasma, or other bodily fluids prior to final installation of the filler piece. Such soaking may help to promote ingrowth of natural bone.

Kit

The invention also includes a kit containing the described aggregate of the described bone void filler pieces. The kit may further include tooling which may be useful during surgery. The kit may further include bone putty or other substances that may be useful during surgery.

Other Aspects of the Invention

For certain applications such as simple geometries, the bone void filler pieces could also be manufactured by molding, or by other method. The invention also includes bone void filler pieces manufactured by any of the described methods.

After any method of manufacturing the matrix of the bone void filler piece, it is possible to apply one or more bioactive substances to the matrix of the bone void filler piece such as by dispensing or dipping. In still other aspects of the invention, the deposited powder used in three-dimensional printing manufacturing may be or may include polymer particles or particles or aggregates of demineralized bone matrix. Particles of demineralized bone matrix may be in an average size range of approximately 100 to 900 micrometers, and more particularly may be approximately 125 micrometers.

Bone void filler pieces may have overall external dimensions in the range of 5 mm. Other, smaller sizes are also contemplated, such as overall dimensions in the range of 2 to 3 mm. These may be suited to smaller bone voids than the other bone void filler pieces would be suited to.

Additional Comments

The bone void filler pieces may be used for a variety of medical indications including situations that may result from the donation of bone, from trauma, from any surgical removal of bone, the need for reconstruction of bone, spinal surgery, or for any other reason.

In general, surface recesses or channels can be on any surface of the bone void filler pieces. The described invention provides bone void filler pieces that provide the benefits of ceramic as a material or provide the benefit of demineralized bone matrix as a material, while also providing a desired shape and geometric features. The invention also can provide features such as surface recesses or channels, which are believed to promote the ingrowth of natural bone. The ability to consistently provide a defined dimension and geometry of bone void filler pieces may be helpful in achieving consistent results. The ability of the described bone void filler pieces to nest and pack efficiently may be helpful in achieving good bone ingrowth.

Patent applications incorporated by reference include commonly assigned "Methods and apparatus for engineered regenerative biostructures such as hydroxyapatite substrates for bone healing applications," U.S. Ser. No. 10/122,129; "Apparatus, systems and methods for use in three-dimensional printing," U.S. Ser. Nos. 10/189,795; 10/190,333; 10/189,799; 10/189,166; 10/189,153; 10/189,797; and "Bone void filler and method of manufacture," U.S. Ser. No. 60/466,884. All patents, patent applications and publications referred to herein are incorporated by reference in their entirety.

All patents and patent applications and publications cited herein are incorporated by reference in their entirety. The above description of illustrated embodiments of the invention is not intended to be exhaustive or to limit the invention to the precise form disclosed. While specific embodiments of, and examples for, the invention are described herein for illustrative purposes, various equivalent modifications are possible within the scope of the invention, as those skilled in the relevant art will recognize.

Aspects of the invention can be modified, if necessary, to employ the process, apparatuses and concepts of the various patents and applications described above to provide yet further embodiments of the invention. These and other changes can be made to the invention in light of the above detailed description. In general, in the following claims, the terms used should not be construed to limit the invention to the specific embodiments disclosed in the specification and the claims, but should be construed to include all bone void fillers and related implantable medical devices that operate under the claims. Accordingly, the invention is not limited by the disclosure, but instead the scope of the invention is to be determined entirely by the following claims.

From the foregoing it will be appreciated that, although specific embodiments of the invention have been described herein for purposes of illustration, various modifications may be made without deviating from the spirit and scope of the invention. Accordingly, the invention is not limited except as by the appended claims.

The invention claimed is:

1. A bone void filler comprising:
an aggregate of pieces, at least some of said aggregate of pieces having a central region and
a plurality of arms connected to said central region,
wherein in at least some of said aggregate of pieces, a first end surface of said central region and first end surfaces of said plurality of arms form a generally planar first end surface of said piece, and a second end surface of said central region and second end surfaces of said plurality of arms form a generally planar second end surface of said piece, said second end surface being opposed to said first end surface,
said arms being approximately equally spaced around said central region;
wherein said at least some of said aggregate of pieces have an overall length measured so as to include two opposed arms, and
said overall length is less than an overall dimension of a void in a bone, said aggregate of pieces being located in said void in said bone such that said pieces touch others of said pieces in a random orientation relative to each other.

2. The bone void filler of claim 1, wherein at least some of said aggregate of pieces has an overall width, and said overall length and said overall width are within 20% of each other.

3. The bone void filler of claim 1, wherein at least some of said aggregate of pieces has a central region dimension, and said central region dimension is between 20% and 45% of said overall length.

4. The bone void filler of claim 1, wherein at least some of said aggregate of pieces has a prismatic dimension, and said prismatic dimension is between 25% and 65% of said overall length.

5. The bone void filler of claim 1, wherein one-half of said overall length is less than a critical gap dimension for bone healing.

6. The bone void filler of claim 1, wherein at least some of said aggregate of pieces contain surface grooves wherein said grooves are less than 250 microns in laminar depth.

7. The bone void filler of claim 6, wherein said overall length is from approximately 3.2 mm to approximately 4 mm.

8. The bone void filler of claim 6, wherein at least some of said aggregate of pieces has a prismatic dimension of from approximately 1.8 mm to approximately 2.6 mm.

9. The bone void filler of claim 6, wherein said overall length is less than or approximately equal to 5.8 mm.

10. The bone void filler of claim 6, wherein at least some of said aggregate of pieces has a prismatic dimension of less than approximately 3.5 mm.

11. The bone void filler of claim 1, wherein said bone void filler comprises pieces having more than one size, all said pieces having a common shape.

12. The bone void filler of claim 1, further comprising additional pieces of said at least some of said aggregate of pieces, wherein said additional pieces comprise a different central region and a different plurality of arms.

13. The bone void filler of claim 12, wherein said additional pieces are of approximately rectangular prismatic shape.

14. The bone void filler of claim 1, wherein at least some of said aggregate of pieces comprise any calcium phosphate.

15. The bone void filler of claim 1, wherein at least some of said aggregate of pieces comprise a majority of beta tricalcium phosphate.

16. The bone void filler of claim 1, wherein at least some of said aggregate of pieces comprise a majority of alpha tricalcium phosphate.

17. The bone void filler of claim 1, wherein at least some of said aggregate of pieces comprise pores which range in size from approximately 1 micrometer to approximately 800 micrometers.

18. The bone void filler of claim 1, wherein at least some of said aggregate of pieces comprise pores which have a mean pore size of approximately 60 micrometers.

19. The bone void filler of claim 18, wherein at least some of said aggregate of pieces comprise pores which have a pore size distribution whose standard deviation is approximately 12 micrometers.

20. The bone void filler of claim 1, wherein said bone void filler further comprises pieces of demineralized bone matrix.

21. The bone void filler of claim 20, wherein said pieces of demineralized bone matrix have an overall dimension of between 100 micrometers and 900 micrometers.

22. The bone void filler of claim 1, wherein at least some of said aggregate of pieces are sterile.

23. The bone void filler of claim 1, further comprising a container in which said aggregate of pieces is contained.

24. The bone void filler of claim 23, further comprising a container of powdered demineralized bone matrix, suitable so that said aggregate of pieces and said powdered demineralized bone matrix can be mixed.

25. The bone void filler of claim 23, wherein said aggregate of pieces are contained in the container in random orientation.

26. The bone void filler of claim 23, wherein said container comprises a piston and a cylinder slidably disposed with respect to each other.

27. The bone void filler of claim 26, wherein said container is suitable to aspirate bodily fluids into an interior region of said container.

28. The bone void filler of claim 26, wherein said container is suitable to eject at least some of said aggregate of pieces.

29. The bone void filler of claim 26, wherein said container comprises a cap that is removable so as to provide an opening for dispensing said pieces after aspiration.

30. The bone void filler of claim 26, wherein said aggregate of pieces are contained in said cylinder in random orientation.

31. The bone void filler of claim 26, wherein said aggregate of pieces have prismatic surfaces, and wherein said cylinder is configured such that each piece is contained in said cylinder in an orientation such that at least one prismatic surface of each piece touches a prismatic surface of another piece.

32. The bone void filler of claim 31 wherein said aggregate of pieces are contained inside said cylinder such that said pieces can have any angular orientation around a principal axis of rotation perpendicular to said prismatic surface.

33. The bone void filler of claim 31 wherein said aggregate of pieces are contained inside said cylinder such that all said pieces are constrained to have approximately said same angular orientation around a principal axis of rotation perpendicular to said prismatic surface.

34. The bone void filler of claim 1, wherein at least some of said aggregate of pieces comprise ridges on at least some of their surfaces.

35. The bone void filler of claim 34, wherein said ridges are substantially parallel to an edge of said bone void filler piece.

36. The bone void filler of claim 34, wherein said ridges have a transverse surface dimension which is between one-third and one-fifteenth of said width of said surface on which said ridges occur.

37. The bone void filler of claim 34, wherein said ridges have a transverse surface dimension that is between 100 micrometers and 800 micrometers.

38. The bone void filler of claim 34, wherein said pieces comprise random approximately isotropic roughness on at least some surfaces.

39. The bone void filler of claim 34, wherein said pieces comprise ridges on at least some perimetral surfaces and comprise random approximately isotropic roughness on said first end surface of said piece and said second end surface of said piece.

40. The bone void filler of claim 34, wherein said pieces comprise ridges on said end surface planes and on some perimetral surfaces, and comprise random approximately isotropic roughness is on some other perimetral surfaces.

41. The bone void filler of claim 34, wherein said bone void filler further comprises pieces of demineralized bone matrix.

42. The bone void filler of claim 1, wherein at least some of said aggregate of pieces comprise passageways in said pieces.

43. The bone void filler of claim 42, wherein said passageways comprise through-holes.

44. The bone void filler of claim 42, wherein said passageways comprise blind holes.

45. The bone void filler of claim 1, wherein said bone void filler has a bulk packing density greater than 0.5 g/cc.

46. The bone void filler of claim 1, wherein said plurality of arms is four arms.

47. The bone void filler of claim 1, wherein said plurality of arms is three arms.

48. A bone void filler comprising:
an aggregate of resorbable pieces, at least some of said aggregate of pieces having a first planar end surface having a first planar end surface shape and a second planar end surface having a second planar end surface shape, and side surfaces connecting said first planar end surface and said second planar end surface, said second planar end surface shape being congruent to said first planar end surface shape, said first planar end surface and said second planar end surface being parallel with one another;
said at least some of said aggregate of pieces having respective maximum dimensions, and said maximum dimensions being less than an overall dimension of a void in a bone, said plurality of pieces being located in said void in said bone so as to touch others of said pieces in a random orientation relative to each other,
wherein said first planar end surface shape has a perimeter in the form of a polygon defining an interior of said polygon, said polygon comprising a series of line-segment sides defining interior angles at junctions of adjacent pairs of said line-segment sides, said interior angles being measures facing said interior of said polygon, wherein at least one of said interior angles is greater than 180 degrees.

49. The bone void filler of claim 48, wherein at least two of said interior angles are greater than 180 degrees.

50. The bone void filler of claim 49, wherein at least two others of said interior angles are less than 180 degrees.

51. The bone void filler of claim 48, wherein said perimeter has at least six of said sides.

52. A resorbable bone void filler comprising:
an aggregate of pieces,
at least some of said aggregate of pieces comprise a first planar end surface and a longitudinal axis perpendicular to said first planar end surface;
wherein all possible cross-sections parallel to each other and along said longitudinal axis are congruent to each other, and
wherein a perimeter of said first planar end surface forms a polygon defining an interior of said polygon, said polygon comprising a series of line-segment sides defining interior angles at junctions of adjacent pairs of said line-segment sides, said interior angles being measured facing said interior of said polygon, wherein at least one of said interior angles is greater than 180 degrees.

53. The bone void filler of claim 52, wherein said cross-sections through said piece are perpendicular to said longitudinal axis through said piece.

54. A bone void filler comprising:
an aggregate of pieces,
at least some of said aggregate of pieces being shapes formed by a plurality of plane faces;
wherein two of said plane faces lie in parallel planes and are polygons congruent to each other, each of said two polygons defining an interior of said polygon, each of said two polygons comprising a series of line-segment sides defining interior angles at junctions of adjacent pairs of said line-segment sides, said interior angles being measured facing said interior of said polygon, wherein respective perimeters of said two polygons each comprise at least one interior angle greater than 180 degrees; and
wherein the rest of said plane faces are quadrilateral faces.

55. A bone void filler comprising an aggregate of pieces, at least some of said aggregate of pieces having a central region and exactly two non-collinear arms connected to said central region,
wherein each of said arms has a respective planar end most distant from said central region, wherein each of said arms has a respective axis extending perpendicular to said respective planar end surface through a centroid of said respective planar end surface, all of said axes being located in a common plane, wherein each piece has an overall maximum dimension, and said overall maximum dimension is less than an overall dimension of a void in a bone, said aggregate of said pieces being located in said void in said bone such that said pieces touch others of said pieces in a random orientation relative to each other.

56. A bone void filler comprising an aggregate of pieces, wherein at least some of said pieces comprise exactly three arms, wherein each of said arms has a respective planar end most distant from said central region, wherein each of said arms has a respective axis extending perpendicular to said respective planar end surface through a centroid of said respective planar end surface, wherein said three axes are coplanar, wherein said at least some of said aggregate of said pieces fit inside a void in a bone, said aggregate of said pieces being located in said void in said bone such that said pieces touch others of said pieces in a random orientation relative to each other.

57. The bone void filler of claim 56, wherein respective axes of two of said arms are collinear.

58. A bone void filler comprising an aggregate of pieces, at least some of said aggregate of pieces having a shape comprising a central region and exactly three different arms connected to said central region, wherein each of said arms has a respective planar end most distant from said central region, wherein each of said arms has a respective axis extending perpendicular to said respective planar end surface through a centroid of said respective planar end surface, wherein none of said axes is parallel with any other of said axes, and said axes are not coplanar, wherein said at least some of said aggregate of said pieces fit inside a void in a bone, said aggregate of said pieces being located in said void in said bone such that said pieces touch others of said pieces in a random orientation relative to each other.

59. A bone void filler comprising an aggregate of pieces, at least some of said aggregate of pieces having a shape comprising a central region and exactly two arms extending from said central region, wherein each of said arms has a respective planar end surface most distant from said central region, wherein each of said arms has a respective axis extending perpendicular to said respective planar end surface through a centroid of said respective planar end surface, and said axes are non-collinear with respect to each other, wherein said at least some of said aggregate of said pieces fit inside a void in a bone, said aggregate of said pieces being located in said void in said bone such that said pieces touch others of said pieces in a random orientation relative to each other.

* * * * *